US006060603A

United States Patent [19]
Moore

[11] Patent Number: 6,060,603
[45] Date of Patent: May 9, 2000

[54] SYNTHETIC ANTAGONISTS BASED ON ANGIOTENSIN

[75] Inventor: Graham J. Moore, Calgary, Canada

[73] Assignee: PepMetics, Inc., Calgary, Canada

[21] Appl. No.: 08/841,830

[22] Filed: May 6, 1997

Related U.S. Application Data

[63] Continuation of application No. 08/571,678, Dec. 13, 1995, abandoned, which is a continuation of application No. 07/577,367, May 2, 1990, abandoned, which is a continuation-in-part of application No. 07/458,926, Dec. 29, 1989, Pat. No. 5,459,077.

[51] Int. Cl.$^7$ .............................................. C07D 257/04
[52] U.S. Cl. ...................................... 548/252; 548/342.5
[58] Field of Search .................................. 548/252, 342.5

[56] References Cited

U.S. PATENT DOCUMENTS

| | | | |
|---|---|---|---|
| 3,386,026 | 5/1968 | Ponpipom et al. | 260/112.5 |
| 4,355,040 | 10/1982 | Furukawa et al. | 424/273 R |
| 4,485,177 | 11/1984 | Siedel et al. | 436/547 |
| 4,578,361 | 3/1986 | Siedel et al. | 436/547 |
| 4,702,864 | 10/1987 | Magolda et al. | 260/402.5 |
| 4,818,684 | 4/1989 | Edelman et al. | 435/7 |
| 4,818,763 | 4/1989 | Rusch et al. | 514/2 |
| 4,830,961 | 5/1989 | Petty | 435/34 |
| 4,845,075 | 7/1989 | Murray et al. | 514/12 |
| 4,845,132 | 7/1989 | Masuoka et al. | 521/53 |
| 4,849,407 | 7/1989 | Murray et al. | 514/12 |
| 4,853,871 | 8/1989 | Pantoliano et al. | 364/496 |
| 5,015,651 | 5/1991 | Carini et al. | 514/381 |
| 5,073,566 | 12/1991 | Lifer et al. | 514/381 |
| 5,151,435 | 9/1992 | Bagley et al. | . |
| 5,153,197 | 10/1992 | Carini et al. | . |
| 5,177,095 | 1/1993 | Greenlee et al. | 514/384 |

FOREIGN PATENT DOCUMENTS

| | | |
|---|---|---|
| 0263310 | 1/1988 | United Kingdom . |
| 253310 | 1/1988 | United Kingdom . |
| 0257993 | 3/1988 | United Kingdom . |
| 0323844 | 7/1989 | United Kingdom . |
| 323841 | 7/1989 | United Kingdom . |
| 424317 | 10/1989 | United Kingdom . |
| 90/07110 | 12/1988 | WIPO . |
| 90/07111 | 12/1988 | WIPO . |

OTHER PUBLICATIONS

Moore, G. et al, "Structure–desensitization relationships of angiotensin . . . ", Can. J. Physiol. Pharmacol, vol. 63 (1985), pp. 966–971.

Davidson, D. et al, "The Action of Ammonia on Benzil", The J. of Organic Chemistry, vol. 2, No. 1, pp. 319–327, (1937).

Goghari, M. et al, "Structure–Activity Relationships for the Competitive . . . ", Journal of Medicinal Chemistry, vol. 29, No. 6, (1986), pp. 1121–1124.

Matsoukas, J. et al, "Synthesis and Biological Activities of Analogues . . . ", Journal of Medicinal Chemistry, vol. 28, No. 6, (1985), pp. 780–783.

Wong, P. et al, "Nonpeptide Angiotensin II Receptor Antagonist. IV. EXP6155 and EXP6803", Hypertension, vol. 13, No. 5, (May 1989), pp. 489–497.

Kessler, H. et al, "Separation of Cross–Relaxation and J Cross–Peaks . . . ", Journal of American Chemical Society, vol. 109, No. 2, (1987), pp. 607–609.

Moore, G. et al, "Synthesis of Angiotensin II Antagonist . . . ", Journal of Medicinal Chemistry, vol. 22, No. 9 (1979), pp. 1147–1149.

Scanlon, M. et al, "A New Approach to Angiotensin Antagonist: . . . ", Life Sciences, vol. 34, No. 4 (1984), pp. 317–321.

Moore, G. et al, "Angiotensin as a model for hormone–receptor interactions", Bioscience Reports, vol. 5 (1985), pp. 407–416.

Matsoukas, J. et al, "Proton Magnetic Resonance Studies of Angiotensin II . . . ", Archives of Biochemistry and Biophysics, vol. 248, No. 1 (1986), pp. 419–423.

Rauk, A. et al, "Mechanistic Consequences of Charge Transfer Systems . . . ", Biochemical and Biophysical Research Communications, vol. 145, No. 3 (1987), pp. 1349–1355.

Matsoukas, J. et al, "NMR and Mass Spectroscopic Studies of the Competitive . . . ", Spectroscopy Letters, vol. 21, No. 5 (1988), pp. 477–491.

Moore, G. et al, "Methods for Analyzing and Interpreting Cooperatively . . . ", General Pharmacology, vol. 20, No. 2 (1989), pp. 193–198.

Moore, G. et al, "Angiotensin, 'Antipepties': (–)Messenger RNA . . . ", Biochemical and Biophysical Research Communications, vol. 160, No. 3 (1989), pp. 1387–1391.

Sargent, D. et al, "Membrane Lipid Phase as Catalyst . . . ", Proc. Natl Acad. Sci., vol. 83, (1986) pp. 5774–5778.

Surewicz, W. et al, "Conformational Properties of Angiotensin II . . . ", J. Amer. Chem. Soc., 110, pp. 4412–4414 (1988).

Cheatham, S., "Nuclear Magnetic Resonance Spectroscopy in Biochemistry", Journal of Chemical Education, vol. 66, pp. 111–117 (1989).

Bax, A., Practical Aspects of Two–Dimensional Transverse NOE Spectroscopy J. of Magn. Reson., vol. 63, pp. 207–213.

Moore, G. et al. "Kinetics of Acetylation–Deacetylation of Angiotensin II", Int. J. Pept. Prot. Res., vol. 26, (1985), pp. 469–481.

Grinvald, A. et al., "On the Analysis of Fluoresence Decay Kinetics by the Method of Least Squares", Anal. Biochem., vol. 59, pp. 583–598 (1974).

Lampert, R. et al., "Standards for Nanosecond Fluorescence Decay Time Measurements", Anal. Chem., vol. 55, pp. 68–73 (1983).

(List continued on next page.)

Primary Examiner—Yogendra N. Gupta
Attorney, Agent, or Firm—Burns, Doane, Swecker and Mathis LLP

[57] ABSTRACT

Disclosed are methods for modelling the three-dimensional structure (tertiary structure) of a ligand having one or more active sites employing a charge-transfer interaction. Also disclosed is a model for Angiotensin II derived from such method.

1 Claim, 4 Drawing Sheets

OTHER PUBLICATIONS

Matsoukas, J. et al., "Importance of the N–Terminal Domain of the Type II . . . ", *J. Med. Chem.*, vol. 31, No. 7, (1988), pp. 1418–1421.

Otter, A. et al, "Type I Collagen α–1 Chain C–Telopeptide: Solution Structure . . . ", *Biochemistry*, vol. 27, No. 10, pp. 3560–3567, (1988).

Marion, D. et al, Application of Phase Sensitive Two–Dimensional Correlated *Biochem Biophys. Res. Commun.*, vol. 113, No. 3, pp. 967–974 (1983).

Smeby, R. "Conformation of Angiotensin II", *Chemistry and Biochemistry of Amino Acids, Peptides, and Proteins*, vol. 5, Dekker, New York, pp. 117–163, (1978).

Matsokas, J. et al, "NMR Studies on Angiotensin II: Histidine and . . . ", *Biochemical and Biophysical Research Comm.*, vol. 122, No. 1, pp. 434–438, (1984).

Moore, G., "Photoaffinity Labelling of Angiotensin Receptors: Functional . . . ", *Pharmacol. Ther.*, vol. 33, pp. 349–381, (1987).

Matsoukas, J. et al, "Proton Magnetic Resonance Studies of . . . ", *Peptides 1986*, Proc. of the 19th Euorpean Peptide Symp . . ., Ed. D. Theodoropoulos, pp. 335–339.

Heinze, J. et al, *Chem. Ber.*, vol. 101, pp. 3504–3516, (1968).

Hofle, G. et al, "4–Dialkylaminopyridines as Highly Active Acylation Catalysts[1,2]", *Angew Chem. Int. Ed. Engl.*, vol. 17, pp. 569–583, (1978).

Otter, A. et al, "Solution Conformation of N–Acetyl–L–prolyl–L–glutaminyl–. . . ", *J. Am. Chem. Soc.*, vol. 109, pp. 6995–7001, (1987).

Fowler, P. et al, "Calculation of the Magnitude and Orientation . . . ", *Biochemical and Biophysical Research Comm.*, vol. 153, No. 3, pp. 1296–1300, (1988).

Stewart, J. et al, *Solid Phase Peptide Synthesis*, Pierce Chem. Co. (1984).

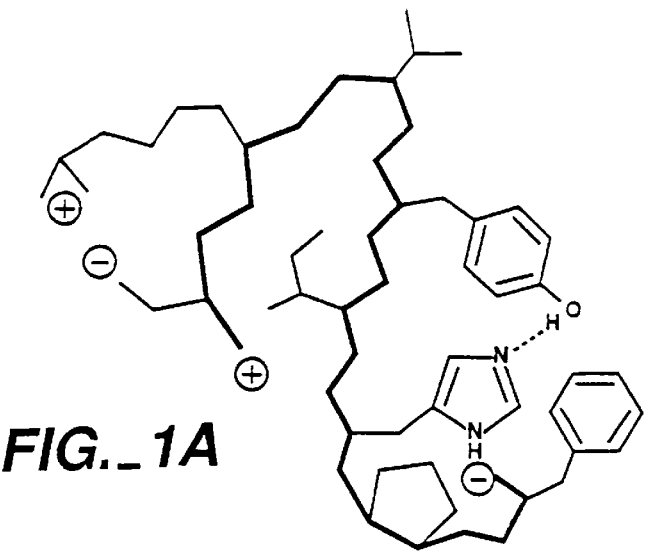
FIG._1A
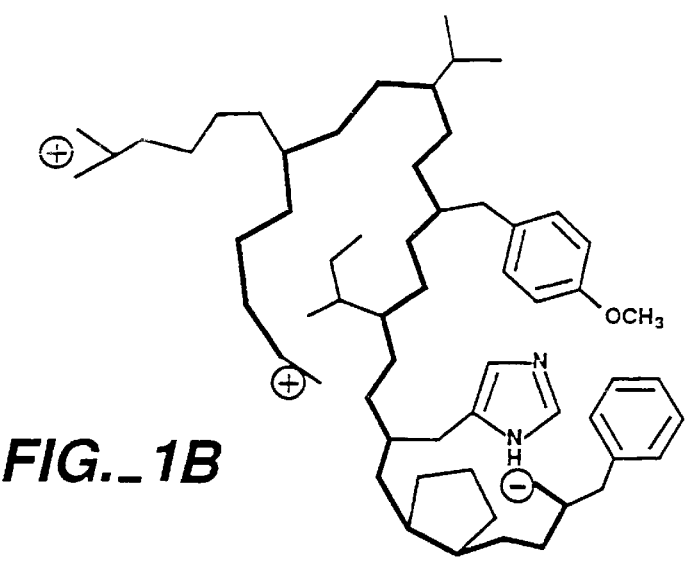
FIG._1B
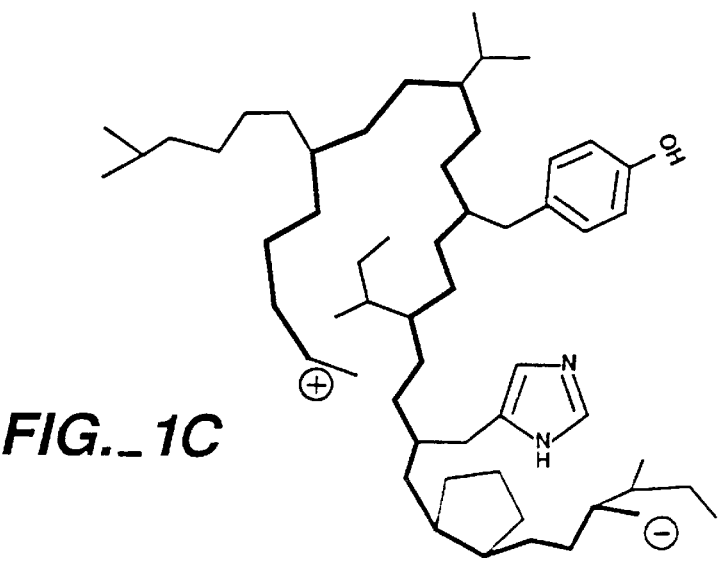
FIG._1C

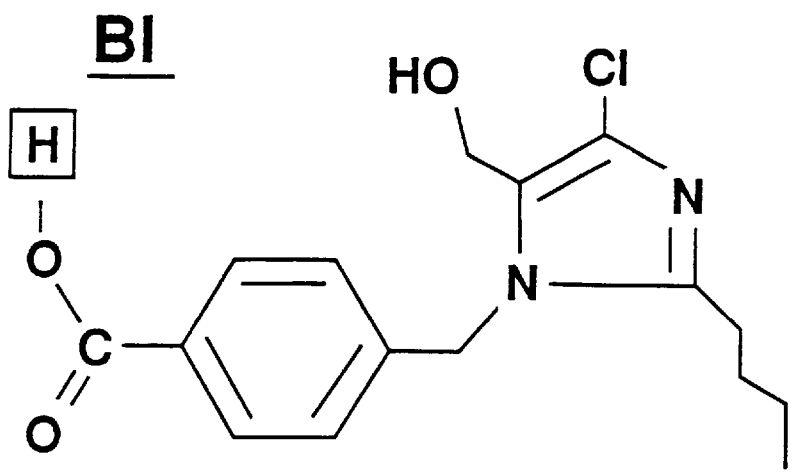
*FIG._2A*
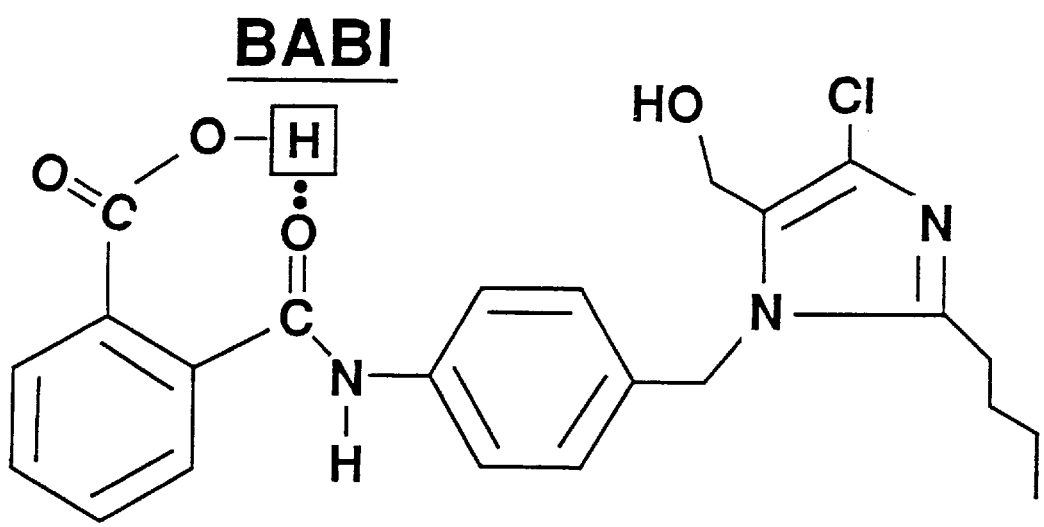
*FIG._2B*

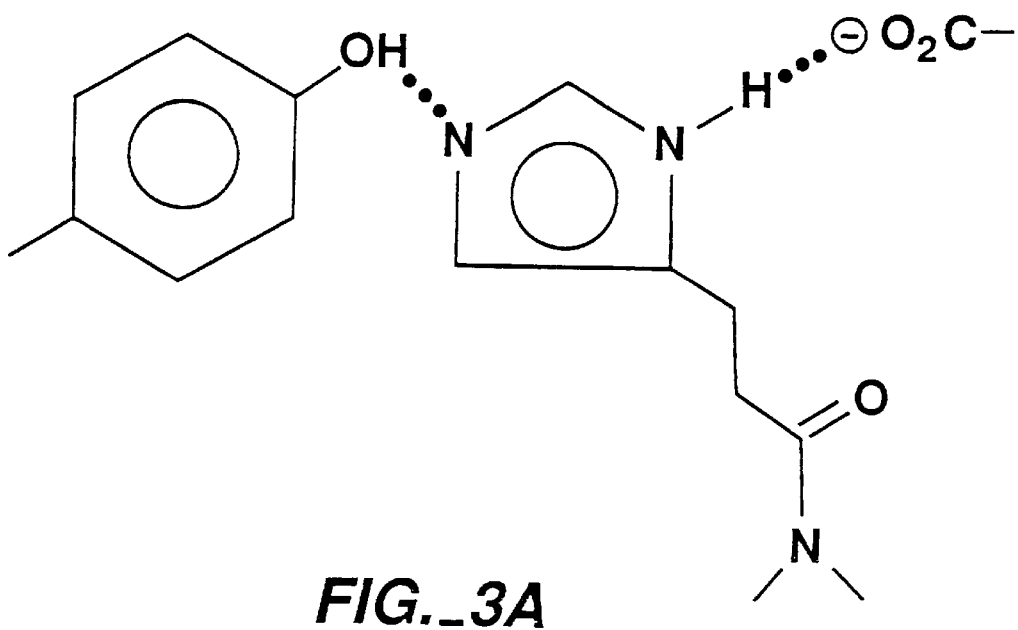
FIG._3A
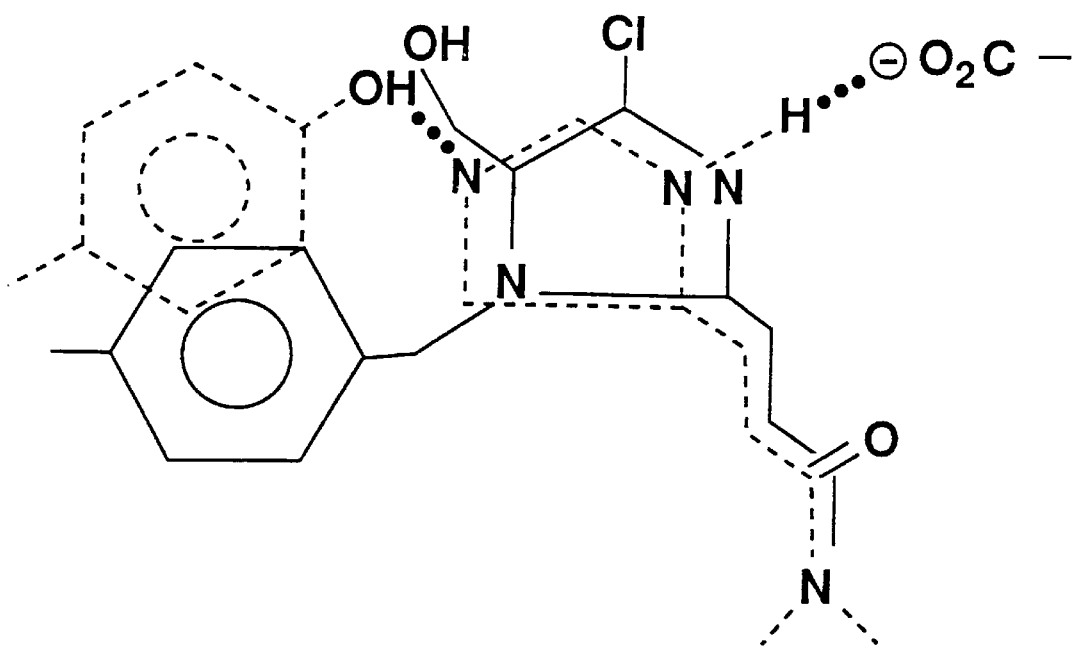
FIG._3B

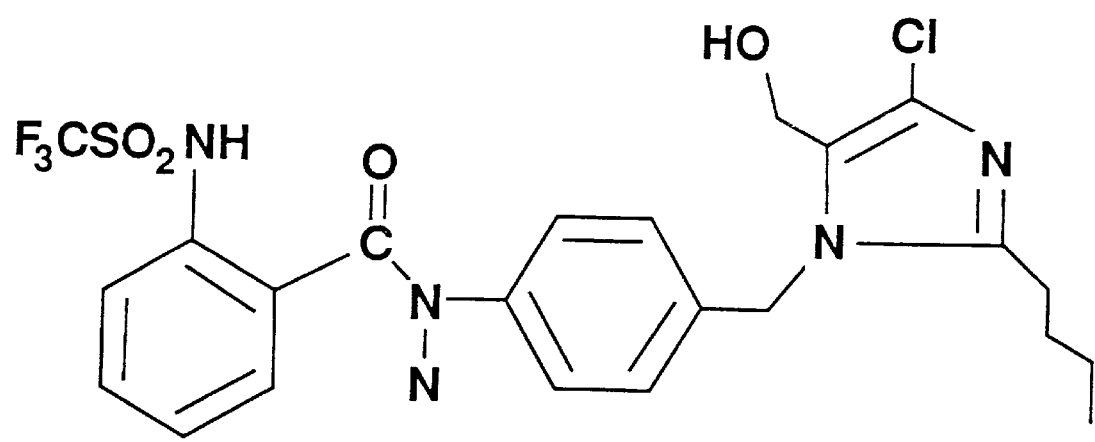
FIG._4

SYNTHETIC ANTAGONISTS BASED ON ANGIOTENSIN

CROSS REFERENCE TO RELATED APPLICATIONS

The present application is a continuation of Ser. No. 08/571,678 filed Dec. 13, 1995, now abandoned, which is a continuation of Ser. No. 07/577,367 filed May 2, 1990, now abandoned, which is a continuation-in-part of Ser. No. 07/458,926, filed Dec. 29, 1989 now U.S. Pat. No. 5,459, 077. The disclosure of U.S. Pat. No. 5,459,077 is incorporated herein by reference.

BACKGROUND OF THE INVENTION

1. Field of the Invention

The present invention is directed to (three-dimensional) structures of biologically active ligands, to methods for designing and synthesizing agonists and antagonists to the ligands based on the three-dimensional models generated for such ligands, and to the model itself generated for Angiotensin II from the methods of this invention.

2. State of the Art

In the field of chemistry, compounds can be defined in several ways. For example, a compound can be defined by its empirical formula, e.g., in the case of n-hexane the empirical formula would simply be $C_6H_{14}$. For simple molecules such as water, methane, carbon dioxide, etc., the empirical formula can provide useful information.

However, as the complexity of the molecule increases, the empirical formula must be complemented by structural information concerning the covalent bonding of the individual atoms vis-à-vis each other in order to derive meaningful information concerning the molecule. Such information is generally depicted as a two-dimensional representation (primary structure) of the covalent bonds between the respective atoms. Such primary structures are well known pictorial representations of the compound of interest. These representations are usually defined as the structural formula of the compound which, for example, in the case of say n-hexane would be represented as:

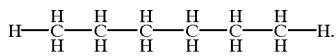

However, even with the molecule's structural formula, valuable information is still missing regarding the position in three-dimensional space of the individual atoms relative to each other. Such three-dimensional structures or conformations for a molecule are determined in part by non-covalent interactions, e.g., electrostatic and non-electrostatic interactions such as ionic interactions, hydrogen bonding, Van der Waal forces, etc., between different atoms of the molecule.

Three-dimensional information, i.e., the ligand's conformation, is extremely valuable for naturally occurring biologically active ligands. In particular, such biologically active ligands generally have one or more active sites on or within the molecular structure of the ligand. Such active sites can involve a charge-transfer interaction (as later defined). When such a ligand is bound to its complementary receptor molecule, the active site activates the receptor molecule thereby affecting the biological activity of the receptor molecule. Thus, activation of the active site, whether by a charge-transfer interaction mechanism or by some other mechanism, is generally a necessary step in affecting the biological activity of the receptor. Further in this regard, if it were possible to create an accurate three-dimensional model of the naturally occurring biologically active ligand [including its active site(s)] as found in vivo, then such models could be used to create mimetics, e.g., agonists and antagonists, of such ligands. For example, if it is desirable to suppress the biological activity of the receptor in vivo, then an accurate three-dimensional model of the receptor's naturally occurring complementary ligand including its active site(s), would greatly facilitate the preparation of antagonists to this receptor. Likewise, an accurate three-dimensional model of the ligand of interest would also facilitate the design and synthesis of agonists when it is desirable to increase or to stimulate the biological activity of the receptor in vivo.

While three-dimensional models have heretofore been proposed for molecules including ligands, such three-dimensional representations have suffered from one or more serious drawbacks, particularly as they relate to biologically active ligands having active site(s) which employ a charge-transfer interaction. In particular, such prior art methods have failed to provide a simple means to identify the active site(s) of such ligands. Accordingly, in such cases, the creation of a three-dimensional model of such a ligand including its active site was generally conducted by extremely laborious procedures such as structure-activity relationships, theoretical considerations, etc. However, because such procedures are unable to identify a charge-transfer interaction at the active site of these ligands, it has not been possible to model mimetics of such ligands to a meaningful conformation.

Additionally, other art recognized methods of modelling the tertiary structure of a compound in three-dimensional space, such as x-ray crystallography, have the drawback that with biologically active ligands, the steps required to prepare the ligand for analysis can change the ligand's tertiary structure and accordingly, the structure as determined by this analysis may not conform to the structure found in vivo. Moreover, not all biologically active ligands are amenable to such analysis.

In view of the above, it is an object of this invention to develop a process which would model the three-dimensional spatial (tertiary) structure of a biologically active ligand having one or more active sites employing a charge-transfer interaction. It is a further object of this invention that this modelling identify the chemical groups at the site(s) of charge-transfer interactions. It is still a further object of this invention to create models of such ligands closely resembling the structure of the ligand found in vivo. It is still another object of this invention to design mimetics to such ligands by reference to the model generated for the ligand. These and other objects are achieved by the present invention as evidenced by the attached summary of the invention, detailed description of the invention, examples and claims.

SUMMARY OF THE INVENTION

The above objectives are achieved by the methods of the present invention. In particular, by using these methods, one is now able to model biologically active ligands having one or more active site(s) which employ charge-transfer interactions. The methods of the present invention involve identification of a charge-transfer interaction using fluorescent methods, identification of the groups involved in the charge-transfer interaction by structure-activity studies, and application of NMR methods to resolve remaining aspects of the conformation surrounding the charge-transfer interaction. Moreover, the model or conformation so obtained is used in a method to design mimetics, i.e., agonist and antagonists, of such ligands. Accordingly, in one of its method aspects, the present invention is directed to a method for creating a three-dimensional spatial model for a biologically active ligand having one or more active sites based on a charge-transfer interaction and further having a known structural formula wherein the three-dimensional spatial assignments for each of the atoms of the ligand in the model are assigned from the steps comprising:

a) determining the presence of charge-transfer interaction(s) in said ligand from fluorescence analysis of said ligand in a fluorescence compatible environment;

b) determining the chemical groups involved in said charge-transfer interaction(s); and c) resolving remaining aspects of the ligand's three-dimensional conformation by obtaining conformational information relative to the active site(s) from nuclear magnetic resonance spectroscopy employing the nuclear Overhauser effect providing that when the nuclear Overhauser effect technique employed in this step is NOESY, then the molecular weight of said ligand is either less than about 500 or greater than about 2000.

Another method aspect of the present invention is directed to a method of modelling antagonists to a biologically active receptor based on the model generated for a biologically active ligand complementary to said receptor wherein said ligand has one or more active sites based on a charge-transfer interaction and further has a known structural formula which method comprises the steps of:

a) creating a three-dimensional spatial model for said ligand by
 i) determining the presence of charge-transfer interaction(s) in said ligand from fluorescence analysis of said ligand in a fluorescence compatible environment;
 ii) determining the chemical groups involved in said charge-transfer interaction(s); and
 iii) resolving remaining aspects of the ligand's three-dimensional conformation by obtaining conformational information relative to the active site(s) from nuclear magnetic resonance spectroscopy employing the nuclear Overhauser effect providing that when the nuclear Overhauser effect technique employed in this step is NOESY, then the molecular weight of said ligand is either less than about 500 or greater than about 2000; and b) identifying a compound having a three-dimensional structure sufficiently similar to said ligand so as to be complementary to said receptor and wherein at least one of the charge-transfer interactions in said compound has been compromised.

Still another method aspect of the present invention is directed to a method of modelling agonists to a biologically active receptor based on the model generated for a biologically active ligand complementary to said receptor wherein said ligand has one or more active sites based on a charge-transfer interaction and further has a known structural formula which method comprises the steps of:

a) creating a three-dimensional spatial model for said ligand by
 i) determining the presence of charge-transfer interaction(s) in said ligand from fluorescence analysis of said ligand in a fluorescence compatible environment;
 ii) determining the chemical groups involved in said charge-transfer interaction(s); and
 iii) resolving remaining aspects of the ligand's three-dimensional conformation by obtaining conformational information relative to the active site(s) from nuclear magnetic resonance spectroscopy employing the nuclear Overhauser effect providing that when the nuclear Overhauser effect technique employed in this step is NOESY, then the molecular weight of said ligand is either less than about 500 or greater than about 2000; and b) identifying a compound having a three-dimensional structure sufficiently similar to said ligand so as to be complementary to said receptor and wherein the charge-transfer interaction(s) in said compound has (have) not been compromised.

Yet another method aspect of the present invention is directed to a method for determining the presence of charge-transfer interaction(s) in the tertiary structure of a biologically active ligand complementary to a biologically active receptor which comprises conducting fluorescence analysis of said ligand in a fluorescence compatible environment.

In a preferred embodiment, the above described methods are particularly suitable for modelling a three-dimensional spatial structure of Angiotensin II. FIG. 6 of this application illustrates a stereo photograph of a molecular model (three-dimensional model) for Angiotensin-II. FIG. 8A of this application illustrates a stereo photograph of a molecular model (three-dimensional) for receptor-bound Angiotensin II. Accordingly, another aspect of this invention is directed to the model of Angiotensin-II illustrated in FIG. 6 as well as the model of receptor-bound Angiotensin II illustrated in FIG. 8A.

A product aspect of the present invention is directed to a compound of the formula:

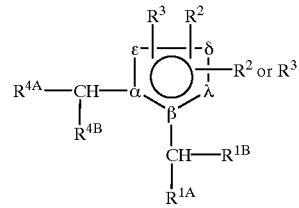

wherein $\alpha$, $f$, $\delta$ and $\epsilon$ are C, N, O or S with the provisos that (a) the ring contains at least one C atom and one N atom, and (b) attachment of R groups is to C or N, and preferably further with the provisos that (c) at least one ring N atom remains unsubstituted, and (d) the pKa of the ring is $\leq 7$ when all attendant groups have been taken into account;

$R^{1A}$, which mimics the structure in angiotensin of

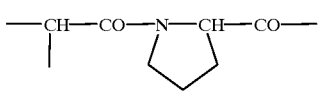

includes the following: —alk; —O—alk; —alk—O—alk; —$CH_2$—CO—$NH_2$; —$CH_2$—CO—NH—alk; —$CH_2$—CO—N(alk)$_2$;

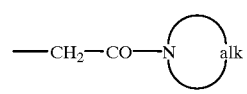

—$CH_2$—CO—AA—$NH_2$; or $CH_2$—CO—AA—Phe, wherein AA is an amino acid preferably proline, azetidine-carboxylic acid, pipecolic acid, nipecotic acid, glycine, alanine, sarcosine, or N-methyl-alanine;

$R^{1B}$, which optionally provides a spacer arm terminating in a mimic of the C-terminal carboxylate group of angiotensin II, includes the following:

preferably with the proviso that when $R^{1B}$ is H, then: (a) if the ring is imidazole either α or γ is other than N, (b) if the ring is other than imidazole either α is C or β is N, (c) $R^{1A}$ comprises a group containing an amide, (d) $R^2$ comprises a group containing A, or (e) $R^3$ comprises a group containing B or is —Asp—Arg—$NH_2$;

$R^2$, which provides steric and/or electronic properties and/or a spacer arm terminating in an acid group, includes the following: —H, —halide; —alk; —O—alk; —$NO_2$; —$CF_3$; —CN; —alk—A; —A;

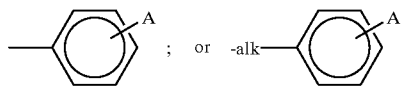

$R^3$, which provides steric and/or electronic properties and/or a mimetic of the tyrosine hydroxyl group of angiotensin II in its "charge relay" conformation, or a spacer arm terminating in a mimic of the N-terminus of N-terminal dipeptide of angiotensin-II, includes the following; —H; —alk; —aryl; —alk—OH; —alk—halide; —$CH_2$—O—alk; —$CH_2$—CN; —$CH_2$—$CO_2H$; —$CH_2CO_2$—alk; —NH—CO—alk; —CO—NH—alk; —alk—B; —CH(OH)—alk—B; —alk—Asp—Arg—$NH_2$; —CH(OH)—alk—Asp—Arg—$NH_2$;

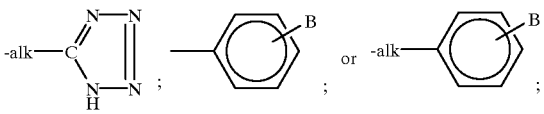

$R^{4A}$, which provides a spacer arm, the relative rigidity of which is an aspect of the design, terminating in an acid group which mimics the tyrosine hydroxy groups of angiotensin II in its "receptor bound" conformation includes the following:

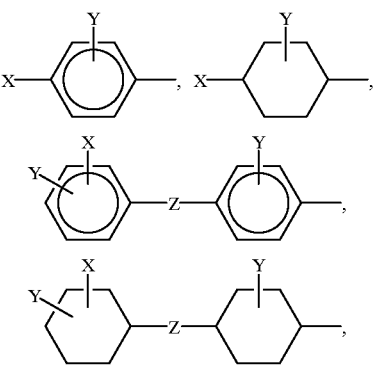

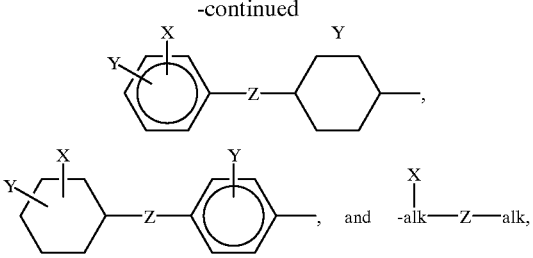

where Z is a bond, —NHCO—, —O—, —$OCH_2$—, or —$CH_2$—; X is —$CO_2H$, —alk—$CO_2H$, —$PO_3H$, —alk—$PO_3H$, —$PO_4H_2$, —alk—$PO_4H_2$, —SH, —alk—SH, —$SO_3H$, —alk—$SO_3H$, —$SO_4H_2$, —alk—$SO_4H_2$, $F_3C$—CO—NH—, $F_3C$—$SO_2$—NH—,

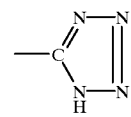

or yet another acid group L H or a pharmaceutically acceptable salt thereof; and Y is —H, —halide, —$NO_2$, —O—alk, —alk, —$CF_3$, or —CN; and $R^{4B}$, which optionally provides a spacer arm terminating in a mimic of the N-terminus or N-terminal dipeptide of angiotensin, includes the following: —H, —alk—B, —alk—Asp—Arg—$NH_2$, —alk—O—alk—B, —alk—O—alk—Asp—Arg—$NH_2$,

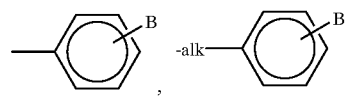

preferably with the proviso that when $R^{4B}$ is H, then: (a) if the ring is imidazole either α or γ is other than N, (b) if the ring is other than imidazole either α is C or β is N, (c) $R^{1A}$ comprises a group containing an amide, (d) $R^2$ comprises a group containing A, or (e) $R^3$ comprises a group containing B or is —Asp—Arg—$NH_2$;

alk=an alkyl group having from 1 to 10 carbon atoms, a cycloalkyl group having 3–6 carbon atoms, an alkenyl group having 2–10 carbon atoms, or an alkynyl group having 2–10 carbon atoms;

halide=—F, —Cl, —Br, or —I;

A=an acid group or its pharmaceutical salt and includes but is not limited to —$CO_2H$, —$CO_2R^+$, —$CO_2$alk, —$SO_3H$, —$SO_4H_2$, —$PO_3H$, —$PO_4H_2$, $F_3$CCONH—, $F_3CSO_2NH$—, —alk—SH, or

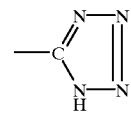

wherein $R^+$ is a lipophilic ester prodrug form such as —$CH_2CO_2C(CH_3)_3$ and the like;

B=a basic group or its pharmaceutical salt including, but not limited to —$NH_2$, —NHalk, —N(alk)$_2$,

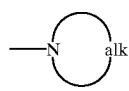

In a particularly preferred product aspect of the present invention, the above five-membered ring is imidazole.

Another product aspect of the present invention is directed to a compound of the formula:

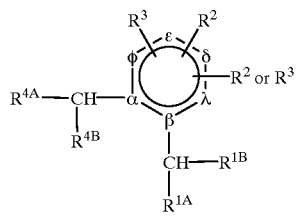

wherein α, β, γ, δ, ε, and φ are C, N, O or S with the provisos that (a) the ring contains at least one C atom and one N atom, and (b) attachment of R groups is to C or N, and preferably further with the provisos that (c) at least one ring N atom remains unsubstituted, and (d) the pKa of the ring is $\leq 7$ when all attendant groups have been taken into account;

and wherein $R^{1A}$, $R^{1B}$, $R^2$, $R^3$, $R^{4A}$, Z, X, and Y, $R^{4B}$, alk, halide, A, and B are as defined previously.

Another product aspect of the present invention is directed to a compound of the formula:

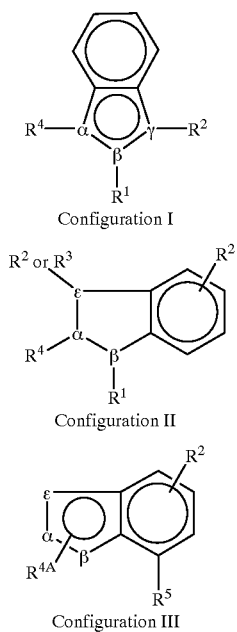

Configuration I

Configuration II

Configuration III wherein α, β, and γ are C or N, with the proviso that only one N atom is substituted. $R^1$ is —CH($R^{1A}$) ($R^{1B}$) and $R^4$ is —CH($R^{4A}$) ($R^{4B}$). $R^5 = R^1$. Substituents $R^{1A}$, $R^{1B}$, $R^2$, $R^3$, $R^{4A}$ and $R^{4B}$ are as defined above, except that for these compounds when $R^{1B}$ is H then (a) $R^{1A}$ comprises a group containing an amide, or (b) $R^1$ is on an N or (c) $R^4$ is on a C.

BRIEF DESCRIPTION OF THE DRAWINGS

FIG. 1A illustrates a two-dimensional representation of the Angiotensin II antagonist, Sarmesin, i.e., [Sar$^1$Tyr(Me$^4$)] Angiotensin II.

FIG. 1B illustrates a two-dimensional representation of the Angiotensin II.

FIG. 1C illustrates a two-dimensional representation of the Angiotensin II antagonist, Sarilesin, i.e., [Sar$^1$Ile$^8$] Angiotensin II.

FIG. 2A illustrates a two-dimensional representation of one example of an N-benzyl-imidazole compound and FIG. 2B illustrates a two-dimensional representation of one example of an N-benzamidobenzylimidazole, both compounds are in a class of compounds which are Angiotensin II antagonists.

FIG. 3A illustrates a two-dimensional structural formula of the imidazole portion of Angiotensin II whereas FIG. 3B provides an overlay of the common portions of the compounds illustrated in FIGS. 2A and 2B and depicted by solid lines onto the imidazole portion of Angiotensin II illustrated in FIG. 3A and depicted by dashed lines.

FIG. 4 illustrates a receptor bound form of Angiotensin II.

DETAILED DESCRIPTION OF THE INVENTION

Although investigations on the conformation of naturally occurring biologically active ligands such as Angiotensin-II have heretofore been carried out, such investigations generally did not take into account the presence of a charge-transfer interaction in the ligand which is required for receptor activation, and therefore it has not heretofore been possible to readily model ligands as well as mimetics of such ligands to a meaningful conformation. However, by the methods of the present invention which do take into account charge-transfer interactions, it is now possible to model biologically active ligands having active site(s) which employ charge-transfer interactions to a meaningful conformation. Moreover, it is also possible to use the methods of the present invention to model mimetics of such ligands. However, prior to discussing this invention in detail, the following terms will first be defined.

"Charge-transfer interaction"—is an electrostatic interaction involving a phenol residue in which an anionic charge is transferred from a charged group to an uncharged group. In one embodiment, the phenol residue is initially uncharged, i.e., phenol, and as a result of the charge-transfer interaction, this residue accepts an anionic charge from another charged group; thus in this embodiment the phenol residue becomes a phenolate residue. In another embodiment, the phenol residue is initially charged, i.e., phenolate, and as a result of the charge-transfer interaction, this residue transfers its anionic charge to an originally uncharged group; thus in this process, the phenolate residue becomes a phenol residue.

Any phenol residue found in a biologically active ligand can be employed in the charge-transfer interaction. Suitable phenol residues include those found in the amino acid tyrosine and derivatives thereof, in steroids having a phenol group such as estradiol [estra-1,3,5(10)-triene-3,17,diol] and derivatives thereof, in catecholamines such as norepinephrine and derivatives thereof, in naphthol containing ligands and the like. The above list is not meant to be an exhaustive representation of naturally occurring components employing phenol residues but rather is presented for the purpose of illustrating that such phenol residues can be found in many different biologically active ligands.

"Active sites based on charge-transfer interactions"— refers to activation site(s) in a biologically active ligand (for activating a biologically active receptor) which is (are)

based on an electrostatic interaction involving a phenol residue in which an anionic charge is transferred from a charged residue to an uncharged residue. Accordingly, in such interactions at least one of the residues is either a phenol residue or a phenolate residue. In such ligands, activation of the receptor by the ligand cannot occur without the charge-transfer interaction. Charge-transfer interactions have heretofore been suggested for ligands such as Angiotensin II. See, for instance, Moore et al., Bioscience Reports, 5, pp. 407–416 (1985), which proposed that transfer of a negative charge from the C-terminal carboxylate residue through the imidazole residue of the histidine amino acid to the tyrosine side chain results in the formation of a phenolate species which upon interaction with the receptor activates the Angiotensin II receptor. Such charge-transfer interactions allow the ligand to modify its electrostatic character into a form which allows activation of the receptor.

The charge-transfer interaction need not be an electrostatic interaction confined solely to the ligand but also could involve a transfer of charge from either a residue on the ligand to a residue on the receptor, or from a residue on the receptor to a residue on the ligand, said transfer being a necessary precondition to activation of the receptor by the ligand. For example, the formation of the tyrosinate species on the ligand can be the result of the transfer of an anionic charge from an anionic residue on the receptor. Upon formation of the tyrosinate species, the ligand is then capable of activating the receptor.

The methods of the present invention employ techniques which permit detection of charge-transfer interactions in biologically active ligands or in biologically active ligand/biologically active receptor complexes. These techniques employ a fluorescence analysis discussed below in a fluorescence compatible environment.

"Ligand"—any organic compound for which a receptor naturally exists or can be prepared.

"Biologically active ligand"—a molecule which binds to a biologically active receptor molecule and which directly or indirectly affects the activity of the receptor molecule. Binding of such ligands to the receptor (acceptor) molecule is accordingly a necessary precondition for initiating, terminating, altering or preventing the biological activity in the receptor molecule. Any ligand which affects the biological activity of the receptor molecule is said to be a biologically active ligand. The biologically active ligand can be a substrate, an agonist, an antagonist, an activator, an inhibitor, etc. When a ligand is able to bind to a specific receptor, the ligand and receptor pair are said to be complementary. Examples of biologically active ligands are well documented in the art. Examples of important biologically active ligands include, for example, oxytocin (wherein the presently known complementary receptors are oxytocin receptor and oxytocin-neurophysin), vasopressin (wherein the presently known complementary receptors are the $V_1$ receptor, the $V_2$ receptor, and vasopressin neurophysin), Angiotensin II (where the presently known complementary receptor is known as the Angiotensin II receptor), and the like.

The biologically active ligand can be peptidic or nonpeptidic in nature. Such ligands can be indigenous to the organism where the biologically active receptor is found. When the ligand is one which is naturally occurring in that organism, then that ligand is referred to as a naturally occurring biologically active ligand. On the other hand, the biologically active ligands can be synthetic molecules which are complementary to the biologically active receptor and which affect the biological activity of the receptor. Thus any molecule which is complementary to a biologically active receptor and which affects the biological activity of the receptor, is a biologically active ligand.

When binding of the biologically active ligand to the biologically active receptor and the activation of the active site results in an alteration of the biological activity of the receptor, e.g., initiates, increases, decreases or terminates the biological activity of the receptor, the ligand is said to directly affect the activity of the receptor. On the other hand, a biologically active ligand indirectly affects the activity of the biologically active receptor when the binding of the ligand to the receptor results in an inability to activate the receptor (because the ligand possess a compromised charge-transfer interaction--as in the case of a antagonist).

Activation of the active site of the naturally occurring biologically active ligand/receptor complex is generally accomplished by some sort of chemical interaction within the ligand or between the ligand and the receptor. As noted above, when the chemical interaction involves the transfer of charge from one residue to another wherein one of the residues is either a phenol or a phenolate residue, the interaction is termed a charge-transfer interaction. Such charge-transfer interactions are believed to result in the alteration of the structure of the ligand or the ligand/receptor complex which then activates the receptor. Because such charge-transfer interactions can now be detected by the techniques employed in the present invention, it is now possible to incorporate such interactions into the model created for the naturally occurring biologically active ligand and to create agonists and antagonists to the complementary receptor.

Preferably, when analyzed by nuclear magnetic resonance spectroscopy employing the nuclear Overhauser effect (as defined below), the ligand should have a molecular weight of less than about 15,000 daltons, and more preferably, less than about 10,000 daltons, even more preferably, less than about 5,000 daltons and most preferably, less than about 3,000 daltons. However, in the fluorescence analysis of this invention, any molecular weight biologically active ligand can be employed.

"Angiotensin II"—refers to the biologically active ligand which is an octapeptide represented by the amino acid sequence of Asp-Arg-Val-Tyr-Ile-His-Pro-Phe wherein each of the above abbreviations are art recognized abbreviations for amino acids.

"Oxytocin"—refers to the biologically active ligand which is a nonpeptide represented by the amino acid sequence of Cys-Tyr-Ile-Gln-Asn-Cys-Pro-Leu-GlyNH$_2$
wherein each of the above abbreviations are art recognized abbreviations for amino acids.

"Vasopressin" (arginine vasopressin) —refers to the biologically active ligand which is a nonapeptide represented by the amino acid sequence of Cys-Tyr-Phe-Gln-Asn-Cys-Pro-Arg-GlyNH$_2$
wherein each of the above abbreviations are art recognized abbreviations for amino acids.

"Receptor"—a molecule which binds the ligand.

"Biologically active receptor"—a molecule, having a specific binding site for its complementary ligand, and can include classical hormone receptors, binding and/or transport proteins, enzymes, antibodies and the like. One embodiment of a biologically active receptor includes membrane bound proteins which control certain cellular processes and which themselves are regulated by the binding (or lack of binding) of its complementary naturally occurring biologically active ligand. Because such membrane bound biologically active receptors are bound to membrane, it is believed that the conformation of the biologically active ligand necessary to activate such receptors are lipid induced. See, for instance, Sargent et al., Proc. Natl. Acad. Sci. (U.S.A.), 83(16), pp. 5774–5778 (1986) and Surewicz et al., J. Amer. Chem. Soc., 110, pp. 4412–4414 (1988). On the other hand, there are other biologically active receptors which are not membrane bound. In such cases, such receptors may not require a lipid induced conformation of the biologically active ligand and, in fact, may require an aqueous induced conformation of the complementary biologically active ligand in order to activate such receptors.

Examples of biologically active receptors have been well documented in the art. Specific examples include insulin receptor (wherein the complementary ligand is insulin), the V1 receptor (wherein the complementary ligand is vasopressin), the V2 receptor (wherein the complementary ligand is vasopressin), oxytocin-neurophysin (where the complementary receptor is oxytocin), the Angiotensin II receptor (wherein the complementary ligand is Angiotensin II), and the like.

"Agonist"—A biologically active ligand which binds to its complementary biologically active receptor and activates the latter either to cause a biological response in the receptor or to enhance pre-existing biological activity of the receptor. The agonist can be the naturally occurring biologically active ligand or it can be a synthetic molecule which can also activate the receptor. For example, it is known in the art that Angiotensin II acts as an agonist for its complementary receptor, the Angiotensin II receptor. Other examples of agonists for the Angiotensin II receptor include [Sar$^1$] Angiotensin II and the like. Examples of agonists for other receptors include norepinephrine (for its complementary receptor the alpha or beta adrenergic receptors). A common characteristic of all agonists in this invention is that the charge-transfer interaction in the agonist which is necessary to activate the biologically active receptor is not compromised. That is to say that the charge-transfer interaction is operable in the agonist.

"Antagonist"—A biologically active ligand which binds to its complementary biologically active receptor and either prevents the activation of the latter or deactivates the latter so as to either prevent or diminish the biological activity of the receptor. For example, it is known in the art that the non-peptides 2-n-butyl-1-[4-carboxybenzyl]-4-chloroimidazole-5-acetic acid) and (methyl 2-n-butyl-1-[4-(2-carboxybenzamido)benzyl]-4-chloroimidazole-5-acetate, sodium salt act as antagonists of the Angiotensin II receptor. See Hypertension, 13, No. 5, May 1989. Other examples of art recognized antagonists to the Angiotensin II receptor include the peptides sarmesin, and the like. Examples of art recognized antagonists to other biologically active receptors include propranolol for the β-adrenergic receptor, cimetidine for the Histamine-H$_2$ receptor and the like. A common characteristic of all antagonists in this invention is that the charge-transfer interaction in the antagonist which is necessary to activate the biologically active receptor is compromised. That is to say that the charge-transfer interaction in the antagonist is impaired and accordingly, the antagonist cannot activate the complementary receptor. For example, one method of impairing the charge-transfer interaction is to modify the hydroxyl group from the phenol moiety by, for example, methylating, (e.g., forming the —φ—O—CH$_3$ group). Another method of impairing the charge-transfer interaction is to remove the hydroxyl group from the phenol moiety, e.g., changing phenol to phenyl.

For example and as noted above, Moore et al., Bioscience Reports, 5, pp. 407–416 (1985), proposed the presence of a charge-transfer interaction in Angiotensin II among the C-terminal carboxylate residue, the histidine amino acid and the tyrosine amino acid. In view of this charge-transfer interaction, two classes of antagonists to Angiotensin II are recognized; both of which have an impaired charge-transfer interaction. The first class involves antagonists in which the tyrosine hydroxyl group is modified or deleted and in which the N-terminal amino acid has been modified (e.g., [Sar$^1$Tyr (Me)$^4$]Angiotensin II, Sarmesin). The other class of antagonists to Angiotensin II involves antagonists in which the C-terminus is modified, with or without concomitant modification of other parts of the molecule (e.g., [Sar$^1$Ile$^8$] Angiotensin II, Sarilesin).

Thus, while an antagonist is a biologically active ligand, it is not a biologically active ligand having an active site based on a charge-transfer interaction because, by definition, this charge-transfer interaction has been impaired.

"Mimetics"—refers to agonists and antagonists to a biologically active receptor but which have a different structural formula (primary structure) than the naturally occurring biologically active ligand for said receptor. That is to say that mimetics are non-naturally occurring biologically active ligands.

"Tertiary structure of a biologically active ligand"—refers to the art recognized term which describes the three-dimensional in vivo organization of the individual atoms of such ligands including the charge distribution map so generated. The tertiary structure of a biologically active ligand (often termed its "conformation") reflects non-covalent interactions between/among atoms as well as covalent bonding between atoms. Non-covalent interactions include both electrostatic and non-electrostatic interactions such as ionic bonds, hydrogen bonding, Van der Waal forces, etc. Because the extent and nature of such non-covalent interactions are dependent on the polarity of the solvent in which they are measured, the tertiary structure (conformation) of such ligands will change when taken from its in vivo microenvironment and placed into an environment of different polarity.

"Fluorescence compatible environment"—is an environment where long lifetime fluorescence (LLF - defined hereinbelow) can be detected. In this regard, it is noted that certain solvents such as dimethylsulfoxide (DMSO) and water do not permit detection of LLF, presumably because of such factors as solvent induced fluorescence quenching, solvent interference with intramolecular hydrogen bond formation. On the other hand, the use of aqueous solutions of micelles and lipid bilayers as well as the use of solvents having a dielectric constant of about 40 or less allows for detection of LLF. Preferably, solvents having a dielectric constant of less than 40 are employed as the fluorescence compatible environment. Even more preferably, the dielectric constant fluorescence compatible environments is from about 2 to about 40. Suitable solvents having a dielectric constant of about 40 or less include, for instance, propylene glycol, isopropanol, trifluoroethanol and the like. Lastly, the solvent so selected should itself not possess fluorescence in the region where the LLF is being detected.

"Receptor-simulating environment"—refers to an environment created to simulate the polarity of the in vivo micro-environment in the immediate vicinity of a biologically active receptor. As noted above, if a biologically active ligand is placed into an environment of different polarity from its in vivo micro-environment, its tertiary structure will change but not its structural formula, i.e., the covalent bonds will not change. The addition of a biologically active ligand into a receptor-simulating environment allows the ligand to substantially conform to the tertiary structure it would possess if placed in the micro-environment of its complementary biologically active receptor. For example and as noted above, for membrane bound biologically active receptors, it is believed that the conformation of a biologically active ligand responsible for activating the receptor is lipid induced. Accordingly, for such receptors, the receptor-simulating environment will be less polar than aqueous environments and solvents having a dielectric constant of about 50 or less have been found to provide a receptor-simulating environment for such membrane bound receptors. Suitable solvents having a dielectric constant of about 50 or less include dimethylsulfoxide (DMSO), trifluoroethanol, isopropanol, propylene glycol, and the like. For non-membrane bound receptors, a solvent having a dielectric constant of about that of water or less will provide a receptor-simulating environment.

"Three-dimensional spatial model of a biologically active ligand"—refers to the tertiary structure of such a biologically active ligand created from the analytical techniques herein described. The creation of such three-dimensional spatial models is sometimes referred to herein as "modelling".

Because the NMR techniques which are employed to create the three-dimensional spatial model employ a receptor simulating environment, the model created will substantially conform to the biologically active ligand's tertiary structure. However, because the polarity of the solvent-simulating environment will not be exactly the same as the in vivo micro-environment, the three-dimensional model will possess minor variations from the tertiary structure. Provided that a receptor simulating environment is employed, the resulting variations will be minor in nature and the three-dimensional spatial model will provide meaningful information concerning the in vivo tertiary structure of the biologically active ligand.

"NMR spectroscopy using the Nuclear Overhauser effect"—refers to the nuclear magnetic resonance methodology which permits insights into the three-dimensional spatial organization of the ligand's atoms. Suitable NMR methodologies include proton [$^1$H] NMR, $^{19}$F NMR, $^{13}$C NMR, and the like. Preferably, proton NMR is employed.

The first step of this methodology employs Correlated Spectroscopy ("COSY") which is a two-dimensional NMR spectrum yielding information on through-bond coupling patterns within a molecule. COSY methodology permits the assignment of individual proton resonances within the spectrum to particular protons in the ligand. This information is then used to identify NOE correlations. Such COSY methodology is well known in the art and is described by Cheatham, Journal of Chemical Education, 66, pp. 111–117 (1989). In some cases, COSY methodology can be supplemented by ROESY and 1-D NOE methodologies in the assignment of individual proton resonances within the spectrum to particular protons in the ligand.

Once the two-dimensional assignments have been made via the COSY methodology, the next step is to conduct nuclear magnetic resonance (NMR) employing the nuclear Overhauser effect methodology [such as one-dimensional NOE enhancement, two-dimensional NOESY and two-dimensional ROESY (rotating frame nuclear Overhauser effect spectroscopy)] on the ligand. NMR employing the nuclear Overhauser effect methodology is used to describe a change in intensity of one NMR line when another line is irradiated at the frequency of the latter line. The change in intensity is due to "through space" energy transfer from one atomic nucleus to another. Thus, the nuclear Overhauser effect provides information of nearest neighbor atomic nuclei to the line that is saturated. Accordingly, the accumulation of a sufficient number of the nuclear Overhauser effects among neighboring atoms can be used to determine the spatial characteristics for the entire molecule.

The nuclear Overhauser effect is a well known and art recognized NMR effect and is described by Cheatham, Journal of Chemical Education, 66, pp. 111–117 (1989). This reference describes the use of one-dimensional NOE enhancement as well as the use of NOE in 2-dimensional NMR (NOESY) as a tool to create three-dimensional models. The ROESY method is also well known and art recognized and is described by Bax and Davis, J. of Magn. Reson., 63, pp. 207–213 (1985). The use of ROESY is particularly suitable for intermediate size molecules such as peptide hormones.

"Fluorescence analysis"—refers to the identification of a charge-transfer system in a biologically active ligand by using a fluorescence instrument capable of measuring fluorescence decay at the level of a nanosecond, or shorter, time intervals. Such equipment is known in the art and is commercially available, for example, from Photochemical Research Associates under the tradename System 3000. Fluorescence decay due to an excited-state phenol (or phenolate) species involved in the charge-transfer interaction is determined in a fluorescence compatible environment after excitation with light of a suitable wavelength. For example, if tyrosine is involved in the charge-transfer interaction so as to result in a tyrosinate species, fluorescence decay due to excited-state tyrosinate emitting at and around 350 nm is determined after excitation with light of a suitable wavelength, e.g., 275 nm. Other excited state species (e.g., ligands with phenol containing groups other than tyrosine) involved in the charge-transfer interaction can also be determined by measuring their fluorescence decay at a suitable wavelength after excitation at an appropriate wavelength. The appropriate wavelengths of absorption and emission can be readily determined by the skilled artisan for any given phenol containing ligand.

The experimentally obtained fluorescence decay, which is described as a sum of exponentials, is deconvoluted, and the lifetime of the longest component due to the phenolate species of interest is determined. Methods for summing the exponentials to obtain the fluorescence decay, deconvolution of the fluorescence decay and determining the lifetime of the longest component due to the phenolate species are known in the art and exemplified in the examples set forth hereinbelow.

Long lifetime fluorescence ("LLF") —is the half-life of the longest living fluorescent component emitting at or around the species' fluorescent maximum and is employed to determine the existence of a stable charge-transfer interaction occurring in the ligand. In particular, in tyrosinate excited-state fluorescence analysis in propylene glycol, LLFs greater than about 11 nanoseconds and preferably greater than about 12 nanoseconds are diagnostic that the tyrosinate moiety or modified tyrosinate moiety is participating in a stable charge-transfer interaction. Such diagnosis is made on the basis that LLF's greater than about 11 nanoseconds for tyrosine or modified tyrosine containing ligands in propylene glycol correlate to the presence of at least some (i.e., ≧1% relative to Angiotensin II) agonist activity for said ligands. On the other hand, a LLF of 11 nanoseconds or less in propylene glycol is indicative that the tyrosinate species or modified tyrosinate species responsible for the LLF is not sufficiently stable and does not activate the receptor. Again, such diagnosis is made on the basis that LLFs of about 11 nanoseconds or less for tyrosine or modified tyrosine containing ligands correlate to inactive or antagonist activity for said ligands (agonist activity of less than 1% relative to Angiotensin II). Similar correlations to determine whether a species different from tyrosine in a ligand is participating in the charge-transfer interaction can be made based on the LLFs of this species or modified species in a variety of ligands correlated to whether the particular ligand is an agonist, is an antagonist or is inactive.

Without being limited to any theory, it is believed that the charge-transfer interaction imparts a level of stability to the excited state of the species (e.g., tyrosine), which permits a longer LLF for the species. Accordingly, longer LLFs correlate to the presence of a charge-transfer interaction which in turn correlate to agonist activity.

Having defined the terms used herein, the invention will now be described in detail.

As noted above, the first step in the preparation of a three-dimensional spatial model of a biologically active ligand having one or more charge-transfer interactions is a fluorescence analysis of the biologically active ligand. That is to say that the ligand is analyzed using fluorescence techniques in order to determine the existence of a charge-transfer interaction. In the following description of this fluorescence technique, Angiotensin II will be employed as a representative ligand. However, it is understood that other biologically active ligands can be analyzed in the same manner as Angiotensin II by using the methods hereinbelow described for Angiotensin II.

Nanosecond time-resolved fluorescence decays of Angiotensin II and analogs thereof were measured by taking advantage of the characteristic fluorescent properties of the excited-state tyrosinate species (other phenolate species would also exhibit similar characteristic properties for their excited-state). In this regard, in order for fluorescence emission from tyrosinate (and other phenolate species) to occur, there must be proton transfer to/from the phenolic hydroxyl group from/to an appropriate acceptor group. Based on the pka's of tyrosine in the ground state (10.4) and in the excited state (less than or equal to about 5.4), photolysis in the excited-state is more efficient.

In particular, nanosecond time-resolved fluorescence decays of Angiotensin II and analogs thereof were measured from the emission at 350 nm due to its excited-state. Long lifetime fluorescence (LLF) was determined for each of these analogs in several solvents of different polarity using N-acetyl-tyrosine-amide as the reference standard. The results of this analysis demonstrate that solvents such as water and DMSO do not allow detection of long lifetime fluorescence in these analogs; presumably because of factors such as solvent induced fluorescence quenching, solvent interference with intramolecular hydrogen bond formation, etc.. On the other hand, use of a fluorescence compatible environment such as aqueous lipid bilayer solutions, micelles in an aqueous environments, and solvents having a dielectric constant of about 40 or less permit the detection of long lifetime fluorescence.

Without being limited to any theory, it is believed that this detection of the long lifetime fluorescence in a fluorescence compatible environment is due to the fact that such environments either do not quench the fluorescence generated by the tyrosinate excited-state and/or do not interfere with intramolecular hydrogen bonding in Angiotensin II.

Additionally, as noted above, that Angiotensin II conformation (tertiary structure) which permits the formation of a charge-transfer interaction will stabilize the tyrosinate excited-state which in turn results in very long lifetime fluorescence. Insofar as the conformation of Angiotensin II is not stagnant but in fact is dynamic (i.e., in a given environment at a given temperature, Angiotensin II is constantly changing conformation both in vitro and in vivo), only that conformation which permits formation of the charge-transfer interaction responsible for receptor activation will result in the formation of a very long lifetime fluorescence. Accordingly, the environment used for determining the presence of a charge-transfer interaction via such fluorescence analysis should be selected to be compatible with the fluorescence analysis and to allow for the presence of that conformation which permits this interaction. Such results are achieved with the fluorescence compatible environment employed in this invention. Preferably, the fluorescence compatible environment will maximize the presence of that conformation of such a biologically active ligand which actives the receptor; but such is not necessary provided that the fluorescence compatible environment permits the presence of a sufficient amount of the conformation of the biologically active ligand which activates the receptor so that its LLF can be detected.

In membrane bound receptors, recent evidence from site-specific receptor mutation studies suggests that small ligands, i.e., ligands having a molecular weight of less than about 3,000 daltons, bind to a site in one of the transmembrane domains of the receptor protein and therefore may have a biologically active conformation which is lipid-induced. In such cases, it is believed (again without being limited to such a theory) that use of solvents of intermediate polarity or less (i.e., having a dielectric constant of about 50 or less), lipid bilayers and micelles provides a receptor environment which simulates the micro-environment which the ligand encounters in the vicinity of such membrane bound receptors. Thus use of a fluorescence compatible environment for biologically active ligands complementary to such receptors provides the additional advantage that such environments should facilitate the maximization of the ligand's conformer responsible for activating the receptor.

Table I below shows the average long lifetime fluorescence values obtained from Angiotensin II and related analogs in isopropanol as well as propane-1,2-diol (propylene glycol). Table I also shows the agonist activity of Angiotensin II as well as for the listed analogs. [The data set forth in Table I below was obtained in a manner similar to that set forth in Examples 1 and 3 set forth hereinbelow].

TABLE I

| | SOLVENT | | | | |
|---|---|---|---|---|---|
| | PROPANE-1,2-DIOL | | ISO-PROPANOL | | AGONIST |
| LIGAND | $LLF^a$ | % LLF | $LLF^a$ | % LLF | $ACTIVITY^b$ |
| A | 20.8 | 19 | 15.5 | 79 | 100 |
| B | 13.1 | 46 | 13.1 | 10 | 27 |
| C | 18.8 | 11 | 9.3 | 11 | 7 |
| D | 14.9 | 13 | 0 | — | $4^c$ |
| E | 16.2 | 10 | 0 | — | $5^c$ |
| F | 9.2 | 6 | 11.6 | 3 | 0.2 |
| G | 6.6 | 35 | 0 | — | less than 0.1 |
| H | 10.6 | 17 | 9.4 | 16 | less than 0.1 |

TABLE I-continued

| | SOLVENT | | | | |
|---|---|---|---|---|---|
| | PROPANE-1,2-DIOL | | ISO-PROPANOL | | AGONIST |
| LIGAND | LLF[a] | % LLF | LLF[a] | % LLF | ACTIVITY[b] |
| I | 10.2 | 8 | 8.5 | 12 | less than 0.1 |
| J | 0 | — | 6.5 | 20 | less than 0.1[d] |
| K | 7.4 | 10 | 10.2 | 14 | 10 |

[a]in nanoseconds
[b]Agonist Activity was measured via a rat isolated uterus bioassay as described by Matsoukas et al., J. Med. Chem., 31, pp. 1418–1421 (1988). Results are reported relative to Angiotensin II wherein Angiotensin II = 100.
[c]Potent receptor antagonist with residual agonist activity.
[d]Potent receptor antagonist.
Ligand A = Angiotensin II
Ligand B = [Sar$^1$His(3-Me)$^6$]Angiotensin II
Ligand C = [Sar$^1$Phe$^6$]Angiotensin II
Ligand D = [Sar$^1$Cha$^8$]Angiotensin II
Ligand E = [Des$^1$Cha$^8$]Angiotensin II
Ligand F = [Sar$^1$Phe—NH$_2$$^8$]Angiotensin II
Ligand G = [Sar$^1$Ala$^6$]Angiotensin II
Ligand H = [Sar$^1$His(1-Me)$^6$]Angiotensin II
Ligand I = [Sar$^1$D-Pro$^7$]Angiotensin II
Ligand J = [Sar$^1$Ile$^8$]Angiotensin II (Sarilesin)
Ligand K = Angiotensin III The preparation of Ligands B–K is well known in the art. See, for instance, Matsoukas et al., Journal of Med. Chem., 31, pp. 1418–1421 (1988).

Sar=sarcosine
Cha=cyclohexylalanine
Des=amino acid residue omitted

In Table I above, % LLF measures the percent of conformer(s) present which give rise to LLF.

The above data demonstrate that strong agonists, Ligands A and B, possess a long lifetime fluorescence in isopropanol of greater than 13 nanoseconds as compared to Ligands possessing either low agonist activity, antagonist activity or inactivity, Ligands C–K. Likewise, in propylene glycol, Ligands (except Angiotensin III) possessing any agonist activity, Ligands A–E, possess a long lifetime fluorescence of greater than 11 nanoseconds, whereas Ligands either possessing no activity or antagonist activity without any residual agonist activity, Ligands F–J, possess a long lifetime fluorescence of 11 nanoseconds or less. Accordingly, prolonged duration of the long lifetime fluorescence correlates to agonist activity which in turn indicates that tyrosine's phenol residue is involved in the charge-transfer interaction responsible for receptor activation.

Contrasted with the readily conducted method of this invention which establishes that tyrosine is involved in the active state of Angiotensin II via fluorescence analysis, the prior art had previously determined that the tyrosine hydroxyl group of Angiotensin II played an important role in receptor activation either by preparing Angiotensin II analogs without tyrosine or by methylating the hydroxy group of tyrosine. It is clear that the process of the present invention is more facile and does not require the synthesis of numerous analogs of Angiotensin II. Moreover, modification of Angiotensin II by removal of amino acids etc., can in fact change the tertiary structure of the analog relative to Angiotensin II such that meaningful conclusions may be difficult to reach.

Once a charge-transfer interaction has been identified in the ligand via the fluorescence analysis of this invention, the next step in the process of preparing a three-dimensional spatial model of a biologically active ligand having one or more charge-transfer interactions is a determination of the chemical groups involved in the charge-transfer interaction. Such a determination can be conducted by using art recognized structure activity relationships. In this regard, these determinations are greatly facilitated by the knowledge that a phenol/phenolate species is involved in the charge-transfer interaction. Accordingly, in those ligands having only one such species (e.g., tyrosine) it is readily apparent that such a species is involved in the charge-transfer interaction.

In general, structure activity relationships are conducted by creating analogs of the ligand of interest by selectively replacing or modifying one of the components of the ligand (e.g., in the case of a peptide, an amino acid), and then determining the LLFs of the analogs. Reduction in the LLF of an analog as compared to the ligand is significant evidence that the component originally found in the ligand and subsequently replaced or modified in the analog plays a role in the charge-transfer interaction. See Ligands F and G in Table I which identify the histidine and C-terminal carboxylate in the charge-transfer interaction in Angiotensin II. Additionally, loss of agonist activity in the analog provides corroborating evidence that the component plays a role in the charge-transfer interaction. In this regard, if the ligand contains two or more phenol/phenolate species, determination which of such species are involved in the charge-transfer interaction can be made by creating analogs in which one of the two or more phenolic groups has been compromised, by for example, methylating the hydroxy group. Analysis of the LLFs and biological activities of such analogs will provide the required information to determine which of the two or more phenolic groups is involved in the charge-transfer interaction.

Once the groups involved in the charge-transfer interaction have been identified, the next step in the process of preparing a three-dimensional spatial model of a biologically active ligand having one or more charge-transfer interactions is to resolve remaining aspects of the ligand's three-dimensional spatial conformation by obtaining conformational information relative to the active site from nuclear magnetic resonance spectroscopy employing the nuclear Overhauser effect.

As noted above, this step first involves the use of COSY methodology which provides information on through-bond coupling patterns within a molecule and allows for the two-dimensional assignment of individual protons in the ligand. The COSY methodology is established in the art. After the two-dimensional assignment of the individual protons via COSY methodology, the ligand is then examined by conducting nuclear magnetic resonance employing the nuclear Overhauser effect methodology. Suitable nuclear Overhauser effect methodologies include one-dimensional NOE enhancement, two-dimensional NOESY and two-dimensional ROESY. All of these nuclear Overhauser effect methodologies are established in the art.

However, with regard to ligands having a molecular weight of between about 500 to 2000 daltons, the use of NOESY methodology often fails for such ligands, irrespective of the internuclear distances involved, because the tumbling rate for these solutes is close to that at which the maximum possible NOE passes through zero. See Bax and Davis, J. Magn. Reson., 63, pp. 207–213 (1985). Consequently, sequential assignments and the observation of interproton distances revealing structures are impossible using NOESY for such ligands. However, such ligands can be structurally analyzed using either one-dimensional NOE enhancement or ROESY methodologies.

In further regard to nuclear magnetic resonance spectroscopy using the nuclear Overhauser effect, there is a practical limit on the molecular weight of the ligand being analyzed. In particular, ligands having a molecular weight of about 15,000 daltons or greater impose to much complexity on current NOESY/ROESY methodologies to permit their use. However, in certain circumstances, one-dimensional NOE methodologies could be used. Accordingly, in this invention, ligands being investigated by nuclear magnetic resonance spectroscopy employing the nuclear Overhauser effect preferably have a molecular weight of less than about 15,000 daltons and preferably have a molecular weight of less than about 10,000 daltons.

The solvents used when conducting proton nuclear magnetic resonance spectroscopy employing the nuclear Overhauser effect are selected so as to provide a receptor simulating environment. Thus, if the biologically-active receptor is a membrane bound receptor, current hypotheses suggest the role of lipid-induced peptide folding in peptide hormone-receptor interactions. See Sargent et al., Proc. Natl. Acad. Sci. (U.S.A.), 83(16), pp. 5774–5778 (1986); and Surewicz et al., J. Amer. Chem. Soc., 110, 4412–4414 (1988). Such lipid-induced peptides are generally believed to have a molecular weight of less than about 3,000 daltons. Thus, in these circumstances, the use of solvents having a dielectric constant of about 50 or less is justified. Furthermore, such dielectric constants allow for a more ordered peptide structure.

A particularly preferred solvent for use in nuclear magnetic resonance spectroscopy employing the nuclear Overhauser effect for ligands whose complementary receptor is a membrane bound receptor is dimethylsulfoxide (DMSO). In particular, DMSO is preferred because it offers several advantages over other possible solvents having a dielectric constant of about 50 or less for the following reasons: 1) the solvent allows for the buildup of NOEs to a level of detectability which is not possible in solvents such as deuterated water; 2) for the reasons noted above, the bulk dielectric environment provided by DMSO is such that it represents an environment not unlike that encountered by such peptides at their receptors, and which gives useful and practical information; 3) the spectra are characterized by sharp and well resolved proton signals which can be individually assigned using COSY methodology and are often superior to spectra obtained in solvents such as trifluoroethanol, propylene glycol and isopropanol which give broader and often overlapping signals; 4) DMSO is superior to aqueous environments for charged molecules because fewer conformations are usually sampled and conformational averaging is altered in DMSO as compared to water; and 5) the dielectric constant of DMSO (~45) is sufficiently close to the maximum dielectric constant employed in the fluorescence analysis so that minimal conformational changes are expected in the two environments.

When the receptor simulating environment is aqueous in nature, the use of water or a solvent mixture containing water is justified.

In any event, when the NMR methodologies described hereinabove are proton [$^1$H] NMR methodologies, deuterated solvents will be required, i.e., $d_6$-DMSO, $D_2O$ and the like.

Further in this regard and by using the methods of the present invention, molecular models of biologically active ligands have been developed. In particular, FIG. 1 illustrates a molecular model of [Sar$^1$]Angiotensin II. In FIG. 1, the backbone of [Sar$^1$]Angiotensin II is maintained by two gamma turns maintained in part by hydrogen bonds between the Arg CO and Tyr NH and between His CO and Phe NH (not shown). [All of the molecular models depicted herein were developed using Minit Molecular Models, Cochranes, Oxford, U.K. A person skilled in the art can readily reproduce such models.]

For comparison purposes, FIGS. 1A, 1B and 1C illustrate simplified two-dimensional structures showing some conformational aspects of Sarmesin, Angiotensin II and Sarilesin, respectively. In reality, the aromatic rings lie above the peptide backbone.

FIG. 4A of U.S. Pat. No. 5,459,077 illustrates a molecular model of Angiotensin II determined in DMSO/$D_2O$ by 2D-ROESY proton NMR in a manner similar to that of Example 4. The backbone of Angiotensin II is characterized by two gamma turns maintained in part by hydrogen bonds between the Arg CO and Tyr NH and between His CO and Phe NH (not shown). FIGS. 6 and 7 of U.S. Pat. No. 5,459,077 illustrate three-dimensional stereo photographs of the model of Angiotensin II. In regard to the figures containing stereo photographs, is noted that such photographs should be viewed by stereo glasses/viewer in order to obtain the three-dimensional effect. Moreover, the eyepieces of the viewer should be set at 75 mm apart. Such stereo glasses/viewers are commercially available; one source being Marivac, 1872 Garden St. Halifax, Nova Scotia, B3M 3RL, Canada.

Once a three-dimensional spatial model for a biologically active ligand has been developed using the techniques of this invention, further refinement of this model or development of even new models can be accomplished using theoretical considerations. For example, with knowledge of the three-dimensional model for Angiotensin II depicted in FIG. 4A and illustrated in the stereo photographs of FIGS. 6 and 7 of U.S. Pat. No. 5,459,077, it is possible by employing theoretical considerations to create a three-dimensional model for Angiotensin II bound to its receptor, the Angiotensin II receptor. In particular, such theoretical considerations generally relate to readily available chemical pathways. For instance, because of the charge-transfer interaction, the tyrosine hydroxyl group in Angiotensin II has been converted to its tyrosinate species. The tyrosinate species, which is a strong nucleophile, can then be derivatized by the receptor resulting in transient bonding between the ligand and the receptor. Upon such bonding, tyrosine moves away from the histidine side chain because the histidine is no longer able to form a hydrogen bond with the tyrosine hydroxyl group. Moreover, slight repositioning of the histidine is also expected. Such theoretical considerations have already been forwarded. See, for instance, Moore et al., Int. J. Pept. Prot. Res., 26, pp. 469–481, (1985). In view of the above, a receptor bound three-dimensional spatial model of Angiotensin II was developed which accounts for such conformational changes which would occur if Angiotensin II behaves in the suggested manner. A stereo photograph of this model is depicted in FIG. 8A of U.S. Pat. No. 5,459,077.

The validity of the resulting model can be readily verified by overlaying known antagonists onto the receptor bound model and ascertaining whether the antagonists can conform to the model. That is to say that if the model is correct, then the antagonists should be able to adapt a conformation similar to the model of the ligand so as to bind to the receptor and thereby account for their antagonist behavior. In this regard, FIGS. 2A and 2B illustrate examples of compounds from a class (i.e., structurally related compounds) of antagonists of Angiotensin II. This class is generically known as either N-benzyl-imidazole compounds ("BI") or N-benzamidobenzyl-imidazole compounds ("BABI"). It is noted that in FIG. 2B, the acidic proton in BABI is present in a hydrogen bonded form (depicted by the box around this proton together with the dots to the amido carbonyl group) somewhat analogous to the hydrogen bonded form of the tyrosinate species of Angiotensin II. Many acidic groups can exist in similar hydrogen-bonded stabilized forms in BABI compounds, e.g., carboxylate (shown), sulfate, trifluoromethylsulfonamido, and the like. It is also noted that for the BI class of compounds, the acidic proton can occupy a similar position in space to the acidic proton shown in BABI, but that the former is not stabilized by hydrogen bonding.

In FIG. 3B, the common portion of these antagonists have been overlaid onto the imidazole portion of Angiotensin II depicted in FIG. 3A which additionally shows the relative position of the components responsible for the charge-transfer interaction in Angiotensin II (note —the imidazole double bonds have been removed from FIG. 3B for the sake of clarity). In FIG. 3B, the fact that the hydroxyl group of the hydroxymethyl in both antagonists is similarly located to the tyrosine hydroxy group in Angiotensin II; the fact that the n-butyl side chain of both antagonists mimics precisely the His $C_\beta$-His $C_\alpha$-His CO-Pro N chain of Angiotensin II; and the fact that the chlorine atom in these antagonists can serve to decrease the basicity of the imidazole nucleus of these compounds, indicates that the antagonist can form a conformation with similar electronic and three-dimensional characteristics as the conformation of Angiotensin II required for generation of the charge-transfer interaction responsible for activating the receptor. However, because these antagonists lack the necessary functionality to generate a charge-transfer interaction, they can not activate the receptor which accordingly explains their antagonist properties.

Having generated a model for the tertiary structure of a biologically active ligand, it is now possible to design and synthesize mimetics to this ligand. For example, it is now possible to design and synthesize compounds which are sufficiently similar to the model generated for the tertiary structure of the biologically active ligand so as to be complementary to the ligand's receptor. In this regard, antagonists are created when the compound so designed and synthesized has a compromised charge-transfer interaction whereas agonists are created when the compound so designed and synthesized has an operable charge-transfer interaction, i.e., the charge-transfer interaction is not impaired. With knowledge of the model generated for the tertiary structure of a biologically active ligand, the design and synthesis of agonists and/or antagonists to the ligand's complementary receptor is well within the ability of the skilled artisan.

The present invention also offers a particular advantage in the design and synthesis of new mimetics optionally based on the structure of known mimetics coupled with knowledge of the model generated for the tertiary structure of a biologically active ligand. This particular advantage is especially applicable to designing new mimetics of Angiotensin II, which may or may not be based on the structure of known mimetics.

In particular, structure-activity relationships show that the binding affinity between Angiotensin II and its complementary receptor derives largely from Columbic [ionic] forces originating from complementary charges between Angiotensin II and its receptor. (All FIGURES referred to in this paragraph are to the FIGURES in parent U.S. Pat. No. 5,459,077.) The ionic charges on Angiotensin II are illustrated in FIG. 4B which is based on the model for Angiotensin II depicted in FIG. 4A. In FIG. 4B, N⁻ denotes tyrosinate which relocates upon interaction with the receptor (this is shown in FIG. 8A which is a stereo photograph of receptor bound Angiotensin II). On the other hand, the N-benzyl-imidazole (BI) and N-benzamidobenzyl-imidazole (BABI) class of known antagonists to Angiotensin II [Wong et al., Hypertension, 13, pp. 489 et seq., (1989)] are devoid of many of the charges which cause Angiotensin II to bind tightly to its receptor. Overlay of the imidazole group of the BI and BABI compounds depicted in FIGS. 3A and 3B onto the imidazole group of the model for Angiotensin II depicted in FIG. 5A is illustrated in FIG. 5B. The three-dimensional organization of the chemical groups of BI and BABI compounds is such that these compounds can mimic 1) Angiotensin II, 2) Sarmesin, or 3) Sarilesin. (For example, when the imidazole-based hydroxyl group of BABI compounds is methylated, the resulting oxymethyl group occupies a similar position in space to the oxymethyl group of Sarmesin.) Overlay of a specific BABI compound (depicted in FIG. 8C) onto the receptor bound model of Angiotensin II (depicted in FIG. 8A and in color in FIG. 9A) is illustrated in the stereo photograph of FIG. 8B. As can be seen from FIG. 8B (and in color in FIG. 9B), because the BABI compound has a similar spatial arrangement to the Tyr-Val-His sequence of Angiotensin II (as well as to Sarilesin), the BABI compounds can mimic this portion of the model of Angiotensin II (and Sarilesin) so as to be complementary to the Angiotensin II receptor. Further in this regard and without being limited to any theory, it is believed that the receptor may transiently acylate, or the like, the tyrosine hydroxyl group of receptor bound Angiotensin II and alter the location of the tyrosine side-chain relative to its position in the "charge-transfer interaction" form of Angiotensin II. Moreover, it is further believed that the acidic portion of BABI compounds which is stabilized in a predisposed or "preactivated" form by a hydrogen bonding interaction with the carbonyl oxygen of the amido group (See FIG. 3B), occupies a position in space which is similar to that of the tyrosine hydroxyl group in the receptor bound model for Angiotensin II depicted in FIG. 8A. It is still further believed that a bond, similar to that formed between the "preactivated" tyrosinate group of Angiotensin II and a receptor-based acceptor group, will also be formed between the "preactivated" acid group of BABI compounds and the receptor. In contrast to Angiotensin II, it is also believed that for the case of BABI compounds, this will not result in receptor activation because of the different conformational constraints and the nature of the ligand-receptor bond. Thus, for example, if the receptor acylates the tyrosine OH group of Angiotensin II, the adduct formed between Angiotensin II and its receptor will involve an ester bond, whereas that for the BABI compound shown in FIG. 3B will involve an anhydride linkage or for the BABI compound shown in FIG. 8C will involve an amide linkage. This discloses the fact that BABI compounds are Angiotensin II receptor antagonists because they can act as transition state inhibitors or suicide substrates for the Angiotensin II receptor. In contrast to BABI compounds, BI compounds are not likely to act by this mechanism because the acidic proton is not stabilized by hydrogen bonding, and is therefore not preactivated.

In any event, it is seen that the BI/BABI class of compounds commonly possess an imidazole ring which can be modified to enhance the potency of these compounds.

This information, in conjunction with the charge distribution map depicted in FIG. 4B, allows for the design and synthesis of new antagonists to the Angiotensin II receptor based on incorporating additional charges at the appropriate location into BI and BABI compounds so as to increase the binding affinity of these antagonists to the Angiotensin II receptor and accordingly increase their potency. In view of the above, derivatives of the BI and BABI compounds having one or more such charges can be prepared as follows (from FIG. 4B, it can be seen that all charges (except the tyrosinate charge) including the imidazole ring lie in the same approximate plane:

1) All distances are given relative to the center of planar imidazole ring (either of the His amino acid in Angiotensin II or of the imidazole ring of the BI/BABI compounds).

2) The placement of the charges is defined by a line drawn through the center point of the imidazole ring which bisects the $N_3$–$C_4$ bond of imidazole ring of histidine as shown in Formula I as follows:

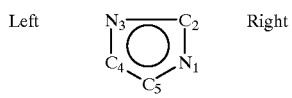

I wherein the subscripts 1–5 correspond to accepted numbering of a histidine imidazole ring. [For analogs in which the His ring is rotated through 180°, e.g., His(3-methyl) analogs, the bisected bond becomes the $N_1$–$C_2$ bond.]

3. One or more of the following charges can be placed onto the imidazole ring:
   i) Direction: Left Charge: Cationic Distance from center of imidazole ring: 7±1.5 Angstroms (Corresponds to N-terminus cationic charge);
   ii) Direction: Right Charge: Anionic Distance from center of imidazole ring: 2.5±0.5 Angstroms (Corresponds to C-terminus anionic carboxylate charge);
   iii) Direction: Left Charge: Anionic Distance from center of imidazole ring: 10±2 Angstroms (Corresponds to aspartic acid anionic charge); and
   iv) Direction: Left Charge: Cationic Distance from center of imidazole ring: 12±2.5 Angstroms (Corresponds to arginine cation)

4. In the above, the orientation of the imidazole rings of Angiotensin II and the BI/BABI compounds is as shown in Formula II as follows:

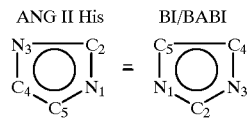

II

Thus $C_4$ in Angiotensin II is equivalent to $N_1$ in the BI/BABI class of compounds.

Examples of side chains which can be added to BI/BABI compounds include for instance compounds of the following Formula III:

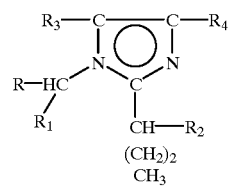

III wherein R is selected from the group consisting of a) phenyl para substituted with a substituent selected from the group consisting of carboxyl or a pharmaceutically acceptable salt thereof, sulfate, and trifluoromethylsulfonamido, and b) —NHC(O)$R_5$ wherein $R_5$ is phenyl ortho substituted with a substituent selected from the group consisting of carboxyl or a pharmaceutically acceptable salt thereof, sulfate, and trifluoromethylsulfonamido, $R_1$ is either hydrogen or hereinafter defined, $R_2$ is either hydrogen or as hereinafter defined, $R_3$ is either hydroxymethyl, —CH$_2$OCH$_3$, —CH$_2$C(O)OCH$_3$, —C(O)OCH$_3$, or as hereinafter defined, and $R_4$ is either fluorine, chlorine or as hereinafter defined.

In view of the above, a compound mimicking the N-terminal cationic charge can be prepared by attaching a suitable amino group at the appropriate location on Formula III. Such a group could be placed at the appropriate distance from the center of the imidazole nucleus by employing an alkyl amino substituent (or another suitable cationic group such as a guanidine group, and the like) wherein the number of methylene groups employed in the chain linking the amino group to the BI/BABI compound is selected so as to provide a positive charge at 7±1.5 Angstroms left from the center of the imidazole ring. For example, placement at $R_3$ of a —(CH$_2$)$_4$—NH$_2$ group will provide such a charge (the amino group will protonate in the in vivo environment to form a —NH$_3^+$ group). Likewise, if hydroxyl functionality is to be maintained at $R_3$, then $R_3$ will be the group —CHOH—(CH$_2$)$_3$—NH$_2$. Alternatively, the positive charge at 7±1.5 Angstroms can be obtained by placement at $R_1$ of a —(CH$_2$)$_3$NH$_2$ group. In still another alternative, $R_1$ or $R_3$ can be —(CH$_2$)$_n$—Asp—Arg—NH$_2$ wherein n is 3 for $R_1$ and 4 for $R_3$ which provides for the 3 charged groups found in the N-terminal dipeptide of Angiotensin II. In regard to the above, only one of $R_1$ and $R_3$ should be substituted at any one time with a cationic group.

A C-terminal anionic mimetic can also be prepared by placing a negative charge at right 2.5±0.5 Angstroms to the center of the imidazole ring. For example, placement at $R_4$ of a —(CH$_2$)$_3$C(O)OH group will provide the necessary negative charge at right 2.5±0.5 Angstroms (the carboxyl group will deprotonate in vivo to provide a carboxylate group, i.e., —C(O)O$^-$. Alternatively, placement at $R_2$ of a —(CH$_2$)$_3$C(O)OH will provide the necessary negative charge at right 2.5±0.5 Angstroms. In regard to the above, only one of $R_2$ and $R_4$ should be substituted at any one time with an anionic group.

Similar considerations regarding the attachment of charges can be applied to the imidazole group of the His amino acid so as to arrive at mimetics to the Angiotensin II receptor. This is particularly true because as indicated above, all of the ionic charges in receptor bound Angiotensin II (except the tyrosinate anion) are in approximately the same plane and moreover, in approximately a straight line. Moreover, the imidazole ring is planar and lies in the same approximate plane as the ionic charges. Accordingly, the substituents set forth above for the imidazole group of BI/BABI compounds could be placed at their equivalent points on the imidazole of the His amino acid.

Similar groups can be designed for the aspartic acid anionic charge and for the arginine cationic charge.

Using the charge distribution map depicted in FIG. 4B, together with the implicit considerations of FIGS. 5 and 8, there are prepared the following new antagonists to the Angiotensin II receptor, based on modifications to the imidazole ring. It should be noted that the nomenclature of the substituents of the ringed compounds is different than that presented above. Thus, the new antagonists to the angiotensin II receptor are compounds of the formula:

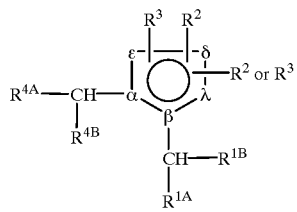

wherein α, β, γ, δ and ε are C, N, O or S with the provisos that (a) the ring contains at least one C atom and one N atom, (b) attachment of R groups is to C or N, (c) at least one ring N atom remains unsubstituted, and (d) the pKa of the ring is $\leq 7$ when all attendant groups have been taken into account;

$R^{1A}$, which mimics the structure in angiotensin of

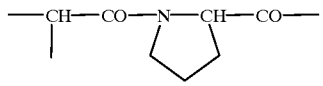

includes the following:
—alk; —O—alk; —alk—O—alk; —CH$_2$—CO—NH$_2$; —CH$_2$—CO—NH—alk; —CH$_2$—CO—N(alk)$_2$;

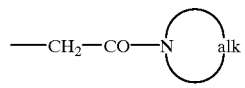

—CH$_2$—CO—AA—NH$_2$; or CH$_2$—CO—AA—Phe, wherein AA is an amino acid (preferably proline), azetidine-carboxylic acid, pipecolic acid, nipecotic acid, glycine, alanine, sarcosine, or N-methyl-alanine;

$R^{1B}$, which optionally provides a spacer arm terminating in a mimic of the C-terminal carboxylate group of angiotensin II, includes the following:

$R^2$, which provides steric and/or electronic properties and/or a spacer arm terminating in an acid group, includes the following: —H, —halide; —alk; —O—alk; —NO$_2$; —CF$_3$; —CN; —alk—A; —A;

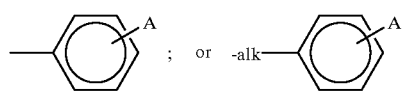

$R^3$, which provides steric and/or electronic properties and/or a mimetic of the tyrosine hydroxyl group of angiotensin II in its "charge relay" conformation, or a spacer arm terminating in a mimic of the N-terminus of N-terminal dipeptide of angiotensin-II, includes the following; —H; —alk; —aryl; —alk—OH; —alk—halide; —CH$_2$—O—alk; —CH$_2$—CN; —CH$_2$—CO$_2$H; —CH$_2$CO$_2$—alk; —NH—CO—alk; —CO—NH—alk; —alk—B; —CH(OH)—alk—B; —alk—Asp—Arg—NH$_2$; —CH(OH)—alk—Asp—Arg—NH$_2$;

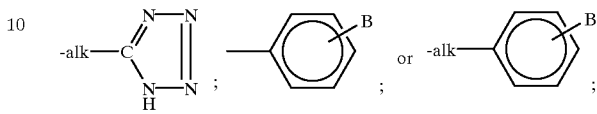

$R^4A$, which provides a spacer arm, the relative rigidity of which is an aspect of the design, terminating in an acid group which mimics the tyrosine hydroxy groups of angiotensin II in its "receptor bound" conformation includes the following:

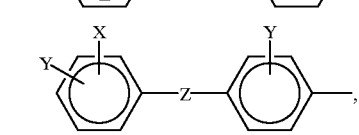

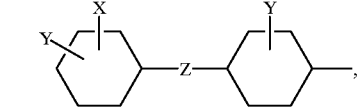

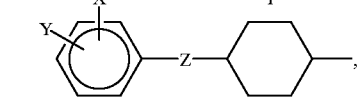

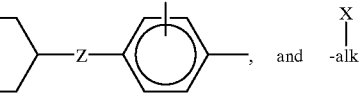

where Z is a bond, —NHCO—, —O—, —OCH$_2$—, or —CH$_2$—; X is —CO$_2$H, —alk—CO$_2$H, —PO$_3$H, —alk—PO$_3$H, —PO$_4$H$_2$, —alk—PO$_4$H$_2$, —SH, —alk—SH, —SO$_3$H, —alk—SO$_3$H, —SO$_4$H$_2$, —alk—SO$_4$H$_2$, F$_3$C—CO—NH—, F$_3$C—SO$_2$—NH—,

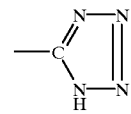

or yet another acid group or a pharmaceutically acceptable salt thereof; and Y is —H, —halide, —NO$_2$, —O—alk, —alk, —CF$_3$, or —CN; and $R^{4B}$, which optionally provides a spacer arm terminating in a mimic of the N-terminus or N-terminal dipeptide of angiotensin, includes the following: —H, —alk—B, —alk—Asp—Arg—NH$_2$,—alk—O—alk—B, —alk—O—alk—Asp—Arg—NH$_2$,

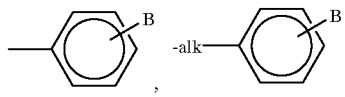

alk=an alkyl group having from 1 to 10 carbon atoms, a cycloalkyl group having 3–6 carbon atoms, an alkenyl group having 2–10 carbon atoms, or an alkynyl group having 2–10 carbon atoms;

halide=—F, —Cl, —Br, or —I;

A=an acid group or its pharmaceutical salt and includes but is not limited to —$CO_2H$, —$CO_2R^+$, —$CO_2alk$, —$SO_3H$, —$SO_4H_2$, —$PO_3H$, —$PO_4H_2$, $F_3CCONH$—, $F_3CSO_2NH$—, —alk—SH, or

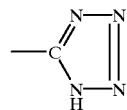

wherein R+ is a lipophilic ester prodrug form such as —$CH_2CO_2C(CH_3)_3$ and the like;

B=a basic group or its pharmaceutical salt including, but not limited to —$NH_2$, —NHalk, —N(alk)$_2$,

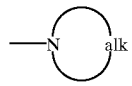

In a preferred aspect of the present invention, when $R^{1B}$ is H, then: (a) if the ring is imidazole either α or γ is other than N, (b) if the ring is other than imidazole either α is C or β is N, (c) $R^{1A}$ comprises a group containing an amide, (d) $R^2$ comprises a group containing A, or (e) $R^3$ comprises a group containing B or is —Asp—Arg—$NH_2$.

In a further preferred aspect of the present invention, when $R^{4B}$ is H, then: (a) if the ring is imidazole either α or γ is other than N, (b) if the ring is other than imidazole either α is C or β is N, (c) $R^{1A}$ comprises a group containing an amide, (d) $R^2$ comprises a group containing A, or (e) $R^3$ comprises a group containing B or is —Asp—Arg—$NH_2$;

In a particularly preferred product aspect of the present invention, the above five-membered ring is imidazole.

Preferably, there is no duplication of $R^2$ or $R^3$ when not equal to H.

In the above formula, the group —CH($R^{1A}$)($R^{1B}$) may be denoted $R^1$ and the group - —CH($R^{4A}$)($R^{4B}$) may be denoted $R^4$. The relative positioning of the R groups set forth above, and particularly the relationship between the $R^1$ group and the $R^4$ group, gives rise to several different configurations in the case of five-membered rings such as imidazole, pyrole, pyrazole, triazoles, tetrazoles, thiazoles, etc.

For example, in the case of imidazole, the following configurations apply:

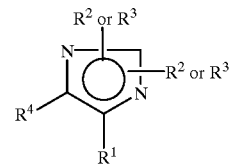

Configuration $N^{\gamma,\epsilon}$

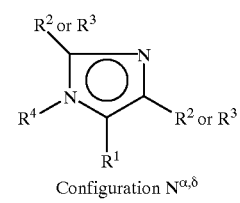

Configuration $N^{\alpha,\delta}$

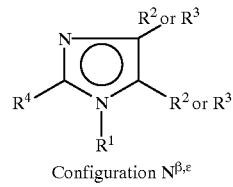

Configuration $N^{\beta,\epsilon}$

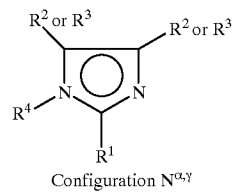

Configuration $N^{\alpha,\gamma}$

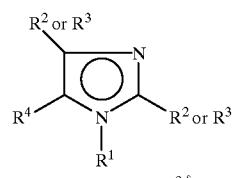

Configuration $N^{\beta,\delta}$

Since $R^4$ is a substituted benzyl group or equivalent, configurations $N^{\alpha,\delta}$ and $N^{\alpha,\gamma}$ are generically speaking N-benzyl compounds, whereas configurations $N^{\gamma,\epsilon\ and\ N\beta,\epsilon}$, and $N^{\beta,\delta}$ are C-benzyl-imidazoles. Similar configurations, numbering ≦5 depending the number of ring N atoms present, apply to other five-membered heterocyclic rings.

The novel antagonists of the present invention are not limited to five-membered rings but indeed encompass six-membered rings including pyridine and diazines (such as, pyrimidine, pyridazine, and pyrazine) as well as triazines. For example, the following may serve as substitute for the imidazole ring in histidine:

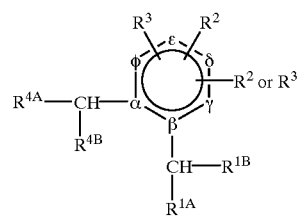

wherein α, β, γ, δ, ε, and φ are C, N, O or S with the provisos that (a) the ring contains at least one C atom and one N atom, (b) attachment of R groups is to C or N, (c) the number of substituted N atoms is one or more, and (d) the pKa of the ring is ≦7 when all attendant groups have been taken into account;

and wherein $R^{1A}$, $R^{1B}$, $R^2$, $R^3$, $R^{4A}$, Z, X, and Y, $R^{4B}$, alk, halide, A, and B are as defined previously.

Preferably, α is other than N.

Preferably, β is N.

Preferably, when $R^{1A}$ or $R^{4B}$ are H, then: (a) if the ring is imidazole either α or γ is other than N, (b) if the ring is other than imidazole either α is C or β is N, (c) $R^{1A}$ comprises a group containing an amide, (d) $R^2$ comprises a group containing A, or (e) $R^3$ comprises a group containing B or is —Asp—Arg—$NH_2$;

Preferably, there is no duplication of $R^2$ or $R^3$ when not equal to hydrogen.

Yet another group of ringed moieties which may be substituted for the imidazole ring of histidine are indoles, benzoazoles, and the like with the further proviso that steric considerations permit that such ring systems fall within the spatial constraints permitted by the conformational models of angiotensin set forth previously. Consideration of these conformational models allows for three general configurations, as follows:

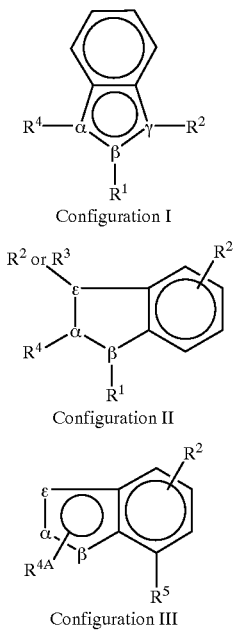

Configuration I

Configuration II

Configuration III wherein α, β, and γ are C or N, with the proviso that only one N atom is substituted. $R^1$ is —$CH(R^{1A})(R^{1B})$ and $R^4$ is —$CH(R^{4A})(R^{4B})$. Substituents $R^{1A}$, $R^{1B}$, $R^2$, $R^3$, $R^{4A}$, $R^{4B}$ and $R^5$ are as defined above, except that for these compounds when $R^{1B}$ is H then (a) $R^{1A}$ comprises a group containing an amide, or (b) $R^1$ is on an N or (c) $R^4$ is on a C. It is noted that configurations I and II-apply to indoles, but not to benzotriazole and benzopyrazole. Configuration I applies to benzimidazole with the proviso that no $R^2$ group is present at $N^γ$, and configuration II applies to benzimidazole with the proviso that no $R^2$ group is present at $N^ε$ and configuration II applies to benzimidazole with the proviso that no $R^2$ or $R^3$ group is present at $N^ε$. Configuration III applies to indoles, benzimidazole, benzopyrazole and benzotriazole; substitution of $R^2$ or $R^3$ at ε is optional according to the above provisos provided that only one nitrogen is substituted.

Equivalent considerations apply to six-membered heterocyclic ring systems such as benzopyridine, benzodiazines, purines, quinolines, phenanthrolines and the like.

According to FIG. 4 of the parent application and considerations relating thereto, one embodiment of the synthesis of new antagonists is based on incorporating additional charges in appropriate locations in BI and BABI compounds so as to increase the binding affinity of these antagonists to the angiotensin II receptor and accordingly increase their potencies. Such considerations apply not only to N-benzyl- and N-benzamidobenzyl-imidazoles but also to C-benzyl- and C-benzamidobenzyl-imidazoles, as outlined in the parent application and in further detail above for 5 configurations of the imidazole ring:

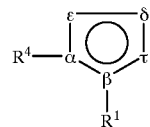

wherein $R^4$=benzyl or benzamidobenzyl which is optionally substituted and wherein α=N or C. According to another consideration inherent to FIG. 5 of the parent application, the synthesis of new antagonists also invokes the inclusion of an improved substitutent to replace the n-alkyl group ($R^1$), namely, a more in angiotesin; such improved mimetics have been outlined above and the following are particularly relevant:

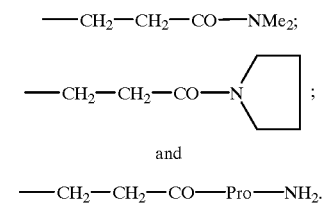

and

—$CH_2$—$CH_2$—CO—Pro—$NH_2$.

In yet another consideration based on FIG. 8 and in particular the discussion outlined on pages 43–46 of the parent application, the orientation of the heterocyclic ring is an important aspect of the design of angiotensin antagonists. As outlined previously, five possible orientations or configurations, which are determined by the placement of the N atoms in the ring relative to the R substituents of the imidazole ring, are applicable to the synthesis of angiotensin antagonists. Furthermore, and as outlined previously, ring systems isofunctional with imidazole can also be present in these antagonists, including other azoles, and including six-membered rings such as pyridine, diazines, and the like, as well as polynuclear ring systems having at least one 5- or 6-membered heterocyclic ring, as described above.

In a preferred embodiment of the present application, the heterocyclic ring is imidazole in any of its five possible configurations outlined previously. A particularly preferred embodiment is configuration $Nγ'^ε$ which gives rise to C-benzyl-compounds and which exactly mimics the imidazole group of the histidine residue of angiotensin-II (See FIG. 5). Furthermore, it is also a preferred embodiment that the $R^1$ substituent is not a straight chain hydrocarbon but contains an amide function mimicking the His-Pro group in angiotensin II. In yet another preferred embodiment, a spacer arm terminationg in a charged group, which mimics the N- or C- terminus of angiotensin II, is incorporated at $R^2$ or $R^3$ or $R^1B$ or $R^{4B}$, as outlined previously. The criteria for these preferred embodiments are based on molecular modelling of angiotensin as outlined in FIGS. 4,5, and 8 and relevant discussion thereto, including pages 43–46 of the parent application, now U.S. Pat. No. 5,459,077).

The compounds depicted above can be readily prepared by the skilled artisan using art recognized techniques. Such compounds and their pharmaceutically acceptable salts are useful as Angiotensin II antagonists. Accordingly, such compounds can be used to control hypertension and/or congestive heart failure in a mammal in need of such treatment. Additionally, the compounds of this invention are contemplated as being useful in other cardiovascular and related diseases such as stroke, myocardial infarction and the like. When used to control hypertension and/or congestive heart failure, the compound is normally administered to such a mammal either orally or parenterally. When so administered, the compound is generally formulated in a pharmaceutically acceptable diluent and at a dosage sufficient to control hypertension and/or congestive heart failure in the mammal so treated. The specific dose levels for such uses can be readily determined by the skilled artisan. Accordingly, the present invention contemplates a method for controlling hypertension in a mammal in need of such treatment which comprises either administering orally or parenterally a pharmaceutical composition of a compound depicted above in an amount sufficient to control hypertension. Additionally, the present invention also contemplates a method for treating congestive heart failure in a mammal in need of such treatment which comprises either administering orally or parenterally a pharmaceutical composition of a compound depicted above in an amount sufficient to control said heart failure. The methods of controlling hypertension are implemented using pharmaceutical compositions comprising a pharmaceutically acceptable carrier and an amount of a compound depicted above effective to control hypertension in a mammal in need of such treatment. The methods of controlling congestive heart are implemented using pharmaceutical compositions comprising a pharmaceutically acceptable carrier and an amount of a compound depicted above effective to control said heart failure.

Methods of preparing the above-described compounds are now described. The synthesis of heterocyclic compounds follows methods well known to one skilled in the art, such as methods described in Comprehensive Heterocyclic Chemistry, Pergamon Press, New York, wherein Vols 4 and 5 (1984) are particularly relevant to the present invention. Synthetic methods of the present invention have also been reviewed in detail in European Patents o263310 and 0323844. In view of the knowledge in the art concerning the synthetic routes employed, general synthetic schemes for the preparation of compounds according to the invention are presented below.. Such schemes generally utilize combinations of chemical transformations together with strategies and protecting groups familiar to one skilled in the art.

Unless otherwise stated, all reactions are conducted at temperatures ranging from 20° C. to the reflux temperature of the solvent for between two hours and two days in a suitably inert solvent such as dimethylformamide, dimethylsulfoxide, chloroform, methylene chloride, benzene, toluene, dioxane, tetrahydrofuran, or ether.

Synthesis of Substituted Imidazoles

The following references are pertinent to the synthesis of substituted imidazoles. Advances in Heterocyclic Chemistry, Vols. 4,12,27,35 (Cambridge University Press) and Heterocyclic Nitrogen Compounds: The Azolesz, K. Schofield et al (1976) Cambridge Univ. Press. A general scheme for the synthesis of substituted imidazoles involves condensation of an amidine or related compound with an α-halo/hydroxy-ketone:

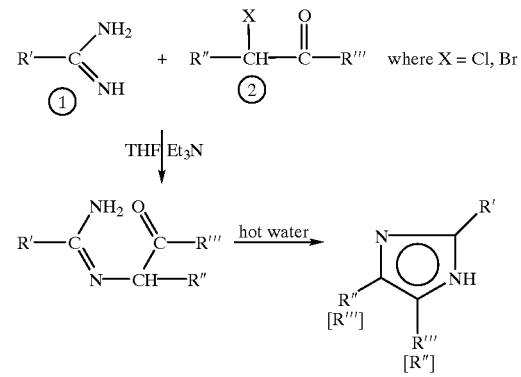

The isomers are separated by conventional methods such as crystallization or chromatography.

The amidine 1 is prepared from the nitrile directly or via the iminoether:

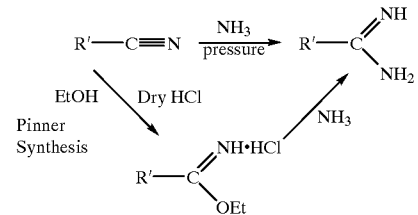

The halo/hydroxy-ketone 2 is prepared by numerous methods known in the art, for example:

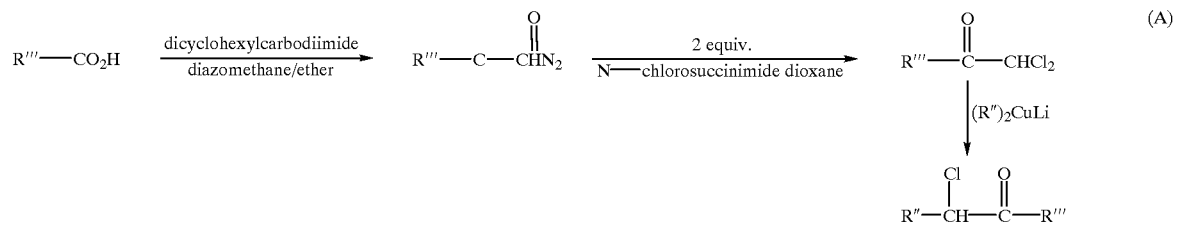

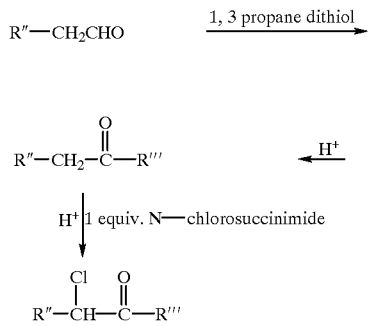

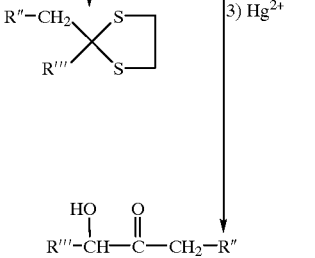

Alternatively, an iminoether can be condensed with an α-hydroxy/halo-ketone in the presence of ammonia:

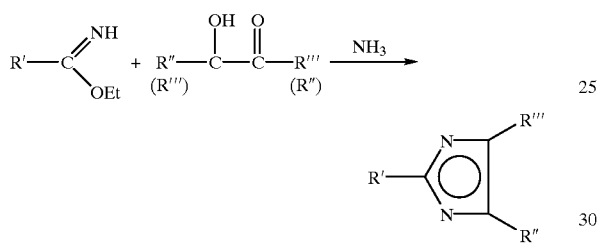

The isomers are separated by crystallization or chromatography.

In another method applicable to substituted N-benzyl compounds in particular, iminoether is reacted with substituted benzylamine to form the amidine which is subsequently condensed with α-halo- or α-hydroxy-ketone/aldehyde:

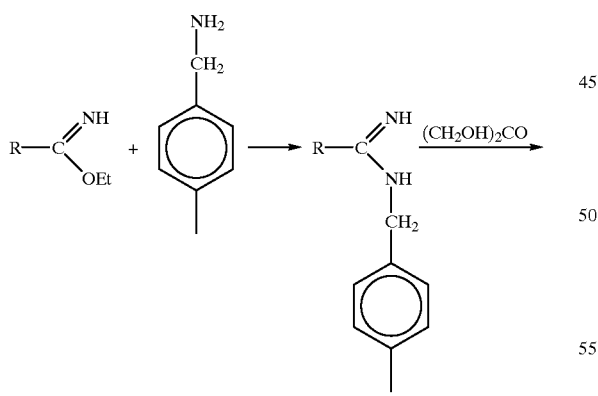

In yet another method applicable to the synthesis of substituted N-benzyl compounds, acylaminoketone is reacted with derivatized benzylamine to form an imine which is then converted to N-benzylimidazole:

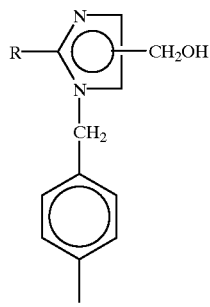

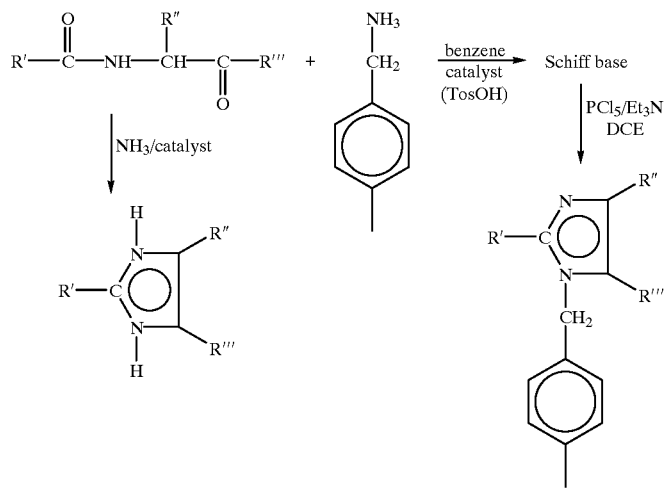

Likewise, imidazole compounds can be obtained using ammonia instead of amine as set forth in Davidson et al, *J. Org. Chem,* 2, 319, 1937 and Heinze et al, *Chem. Ber.* 101, 3504, 1968.

Acylaminoketone is readily obtainable from amino acids using the Dakin-West reaction and modifications thereof as well as from the corresponding α-haloketone by art recognized methods.

Preparation of Acylaminoketones

Aminoacylketones of the general formula

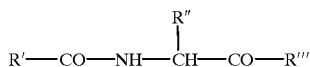

can be prepared frim N-acyl amino acid by reaction with alkyllithium or alkylcopperlithium:

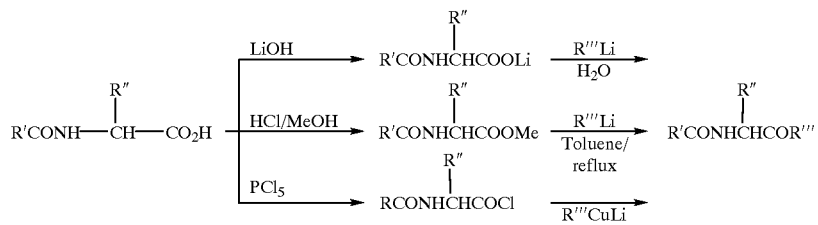

For example, N-acyl-DL-4-nitrophenylalanine can be converted to its butylketone derivative using, e.g., butyllithium.

Another general method for preparing acylaminoketones is by the Dakin-West reaction in which the acyl amino acid is converted to the required acylaminoketone by reaction with anhydride in the presence of base (See Hofle et al, Angew. Chem. Int. Ed. Vol. 17, p. 569, 1978):

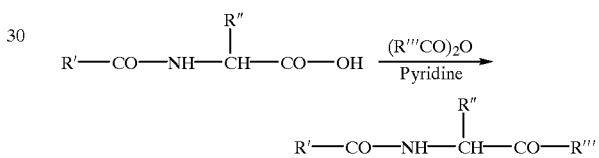

This reaction proceeds through the oxazolinone, and provides an alternative stepwise approach for preparing acylaminoketones when the amino acid is not readily avail able. For example, acylglycine can be converted to other acylamino acids by alkylating the oxazalinone intermediate as follows:

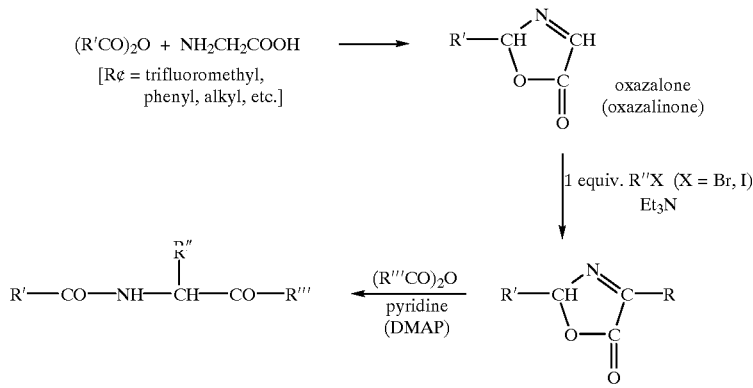

For N-benzyl compounds, alkylation of imidazole nitrogen can be carried out as follows:

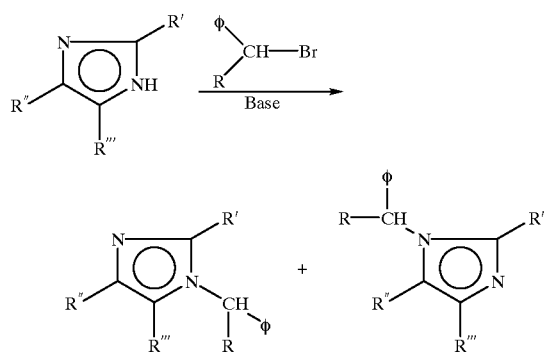

The two products can be separated by classical methods such as crystallization and chromatography.

For C-benzyl compounds, the imidazole nitrogen can be protected with a suitable protecting group such as tosyl, benzyloxymethyl, trityl, or benzyl, which can be subsequently removed by a strategically acceptable method such as acidolysis or hydrogenation. If the protecting group is to be removed at the end of the synthesis, the two products formed do not need to be separated:

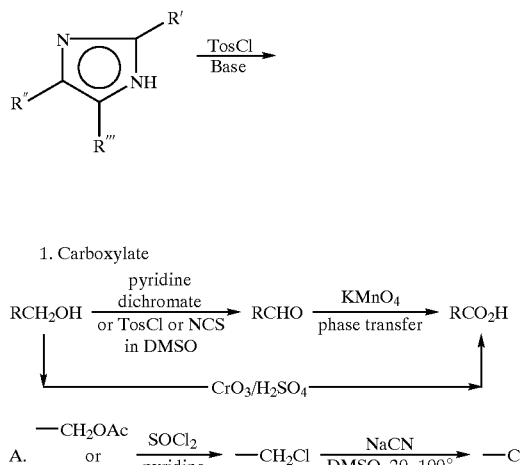

As previously indicated, it is considered to be within the skill of persons in the art to prepare compounds as described. One skilled in the art knows, for example, that it is often not possible to introduce a side group during synthesis in the form which is required in the final product. Thus, for example, an amino group often cannot be introduced in the middle of the synthesis scheme because its reactivity towards electrophiles is high and it could therefore become irreversibly modified during the course of the synthesis to the final product. The amino group is therefore introduced as a nitro group or as an acylamino group or in yet another form in order to circumvent this problem. At or near the end of the synthesis scheme, at which point conversion to an amino group will not compromise the integrity of the final product, the amino group is produced using classical chemical procedures. Similarly, when the end product is to contain a carboxylate function, it is introduced in the form of a nitrile, alcohol, ether, ester, alkene or some other art-recognized precursor.

Conversions of this general type are done by the classical reactions shown below, and produce the side-groups indicated. For further details, see J. March, *Advanced Organic Chemistry*, 1985 J. Wiley & Sons, New York and references therein.

1. Carboxylate $$RCH_2OH \xrightarrow[\text{or TosCl or NCS in DMSO}]{\text{pyridine dichromate}} RCHO \xrightarrow[\text{phase transfer}]{KMnO_4} RCO_2H$$

$$RCH_2OH \xrightarrow{CrO_3/H_2SO_4} RCO_2H$$

A. $-CH_2OAc$ or $-CH_2OH$ $\xrightarrow[\text{pyridine}]{SOCl_2}$ $-CH_2Cl$ $\xrightarrow[\text{DMSO, 20--100°}]{NaCN}$ $-CH_2CN$ $\xrightarrow[\text{50--160° 2--48 hr}]{HCl/AcOH}$ $-CH_2CO_2H$ B. 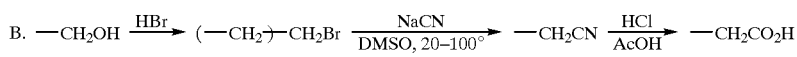
C. 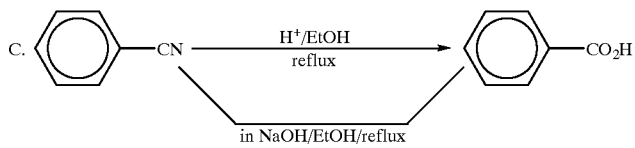
2. Amino
A. 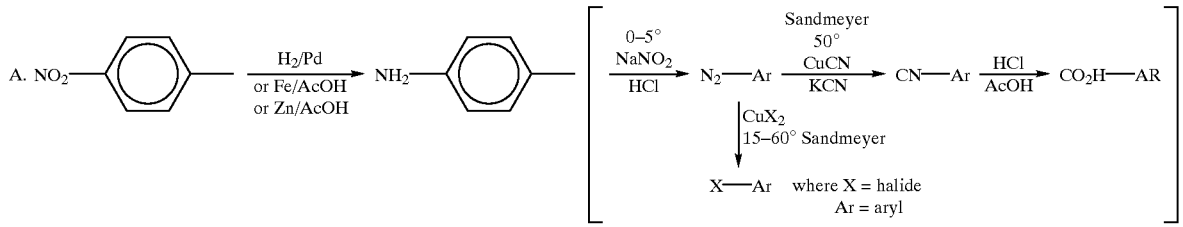
B. —NH—(CO—O—ᵗButyl) $\xrightarrow{\text{TFA}}$ —NH$_2$
Boc (protecting group)
3. Tetrazole
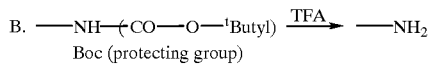
4. Ether
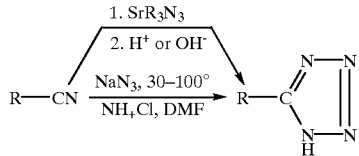
5. Ester
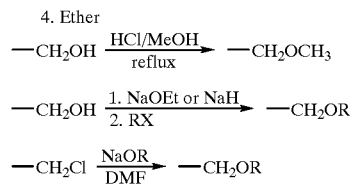
6. Amide
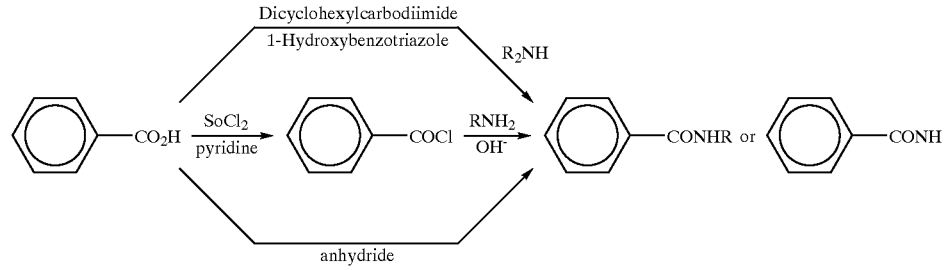
7. Halogenation
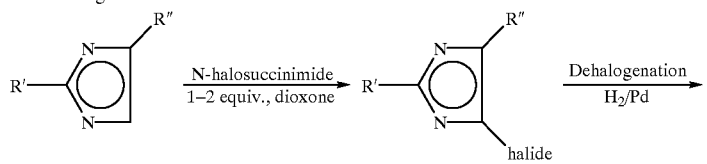
8. Sulfonation/Phosphonation
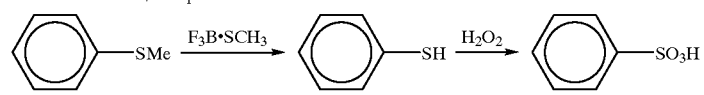

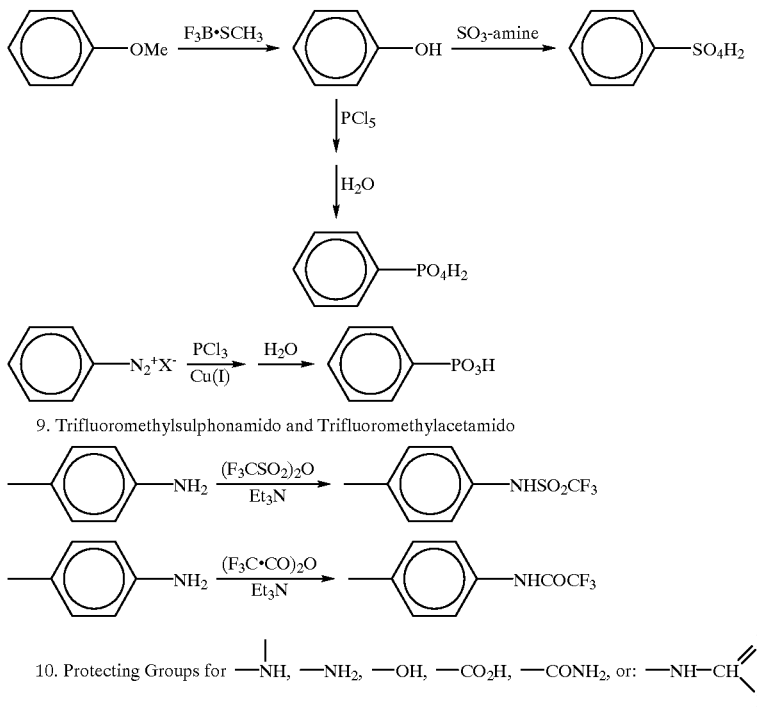

9. Trifluoromethylsulphonamido and Trifluoromethylacetamido

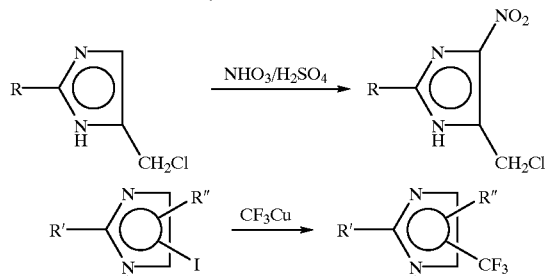

10. Protecting Groups for —NH, —NH$_2$, —OH, —CO$_2$H, —CONH$_2$, or: —NH—CH(=NH)(NH$_2$).

Acid-labile and base-labile protecting groups and protecting groups removable by hydrogenation are well known in the art. Methods for introducing such protecting groups and for their removal are familiar to one skilled in the art as set forth in J. Stewart and J. Young, *Solid Phase Peptide Synthesis*, 1984, Pierce Chem. Co.

11. Nitro and Trifluormethyl

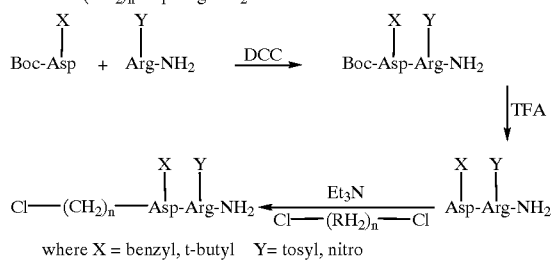

where X = benzyl, t-butyl    Y= tosyl, nitro

In the above reaction, peptide should be added to large excess of cross-linker to avoid dimerization.

Non-imidazole Compounds

As previously indicated, it is possible to employ non-imidazole compounds as new antagonists. Such compounds are prepared by procedures which are analogous to those described above which provide substituents on the ring which can be converted to other groups. Details of methods and strategies for these syntheses have been extensively reviewed in European Patent 0,323,841 for compounds similar to the compounds of the present invention. Consequently, the following is a summary of the more important strategies available to obtain the required compounds, and is not intended to cover the entire field. As with substituted imidazoles, the elaboration of heterocyclic rings derivatized at the ring produces often a mixture of products which can be separated by conventional chromatography methods, and the isomers individually identified by Nuclear Overhauser Effect spectroscopy, and in some cases by bioassay or binding assay, i.e., the ability to displace angiotensin II from its receptor site.

Substituted Pyrole

1. Paal-Knorr reaction: condensation of 1,4 dicarbonyl compounds with ammonia or primary amine, as follows:

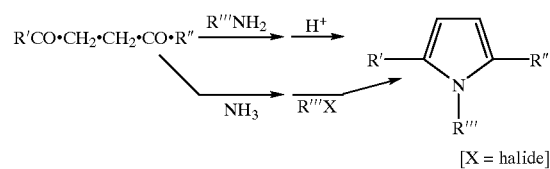

[X = halide]

2. Hantzsch synthesis: condensation of α-haloketones (or α-hydroxyaldehyde or nitroalkenes) with β-ketoesters in the presence of ammonia:

-continued

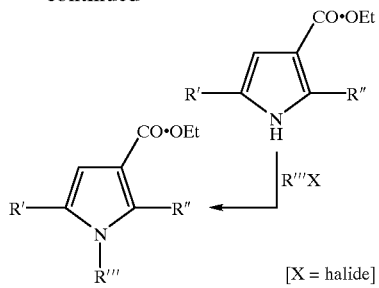

[X = halide]

Substituted Pyrazole:
Condensation of 1,3 dicarbonyl compounds with hydrazine or its derivatives:

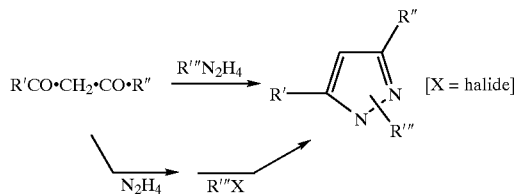

[X = halide]

Substituted 1,2,3-triazole
Thermal cycloaddition of azides to alkynes:

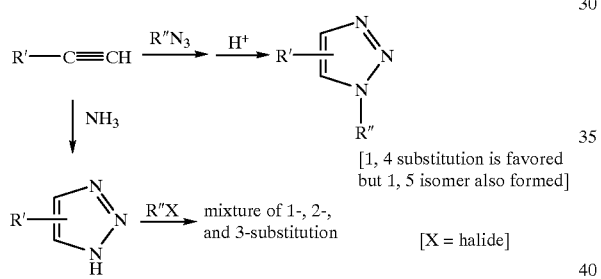

[1, 4 substitution is favored but 1, 5 isomer also formed]
[X = halide]

Substituted 1,2,4-triazole
Reaction of orthoester and acylhydrazine to give 1,2,4-oxadiazole followed by reaction with ammonia or primary amine:

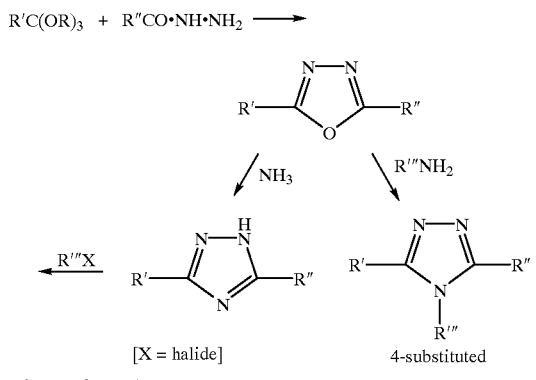

[X = halide]
mixture of 1- and 2-substitution 4-substituted

Substitute Tetrazole
General methods elaborated previously may be applied as set forth concerning protection of tetrazole:

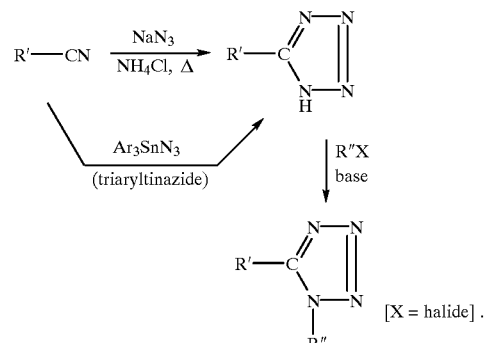

[X = halide].

Substituted Pyridines, Diazines and Triazines are produced by analogous methods. Polynuclear Heterocyclic Compounds Substituted Indoles, Benzimidazole, Benzopyrazole and Benzotriazole Fischer indole synthesis: arylhydrazones of aldehydes or ketones as treated with a catalyst such as ZnCl

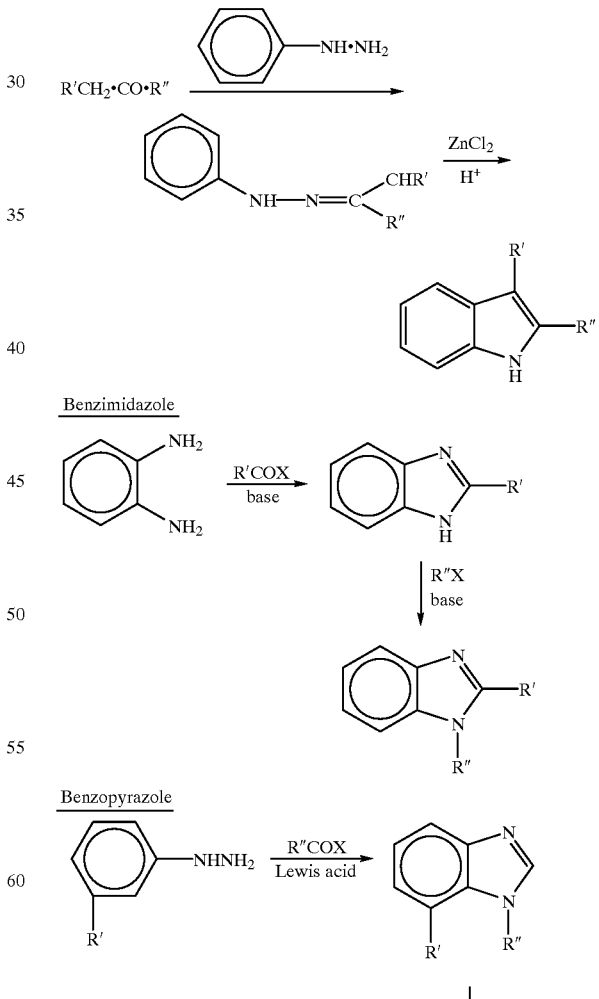

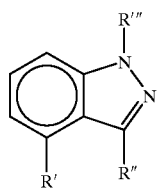
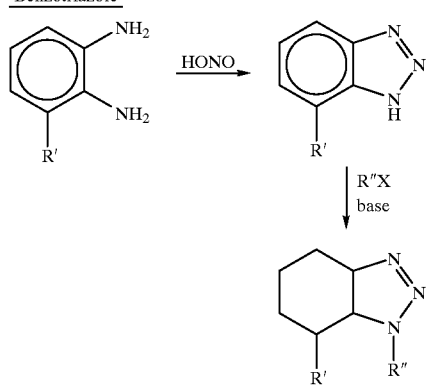

Substituted Benopyridines, Benzodiazines and Benzotriazines are produced by analogous methods.
Compound Synthesis The choice of starting materials and strategy of synthesis of a given compound is dictated by a number of factors including feasibility and cost. The choice of methods and protecting groups and precursor groups for a given synthesis is largely determined by other compromising structural and chemistry factors, which can be satisfactorily ascertained by one skilled in the art.

What is claimed is:

1. A compound of the formula:

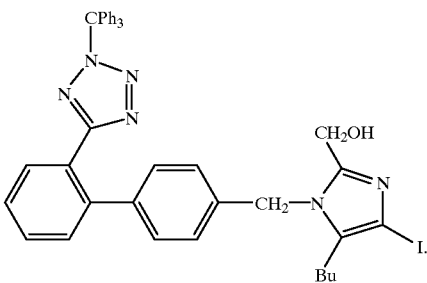

* * * * *